United States Patent
Xia et al.

(10) Patent No.: US 11,299,482 B2
(45) Date of Patent: *Apr. 12, 2022

(54) SALT AND CRYSTAL FORM OF MODIFIED ANDROGRAPHOLIDE COMPOUND AND PREPARATION METHOD THEREOF

(71) Applicants: HEILONGJIANG ZHENBAODAO PHARMACEUTICAL CO, LTD, Heilongjiang (CN); MEDSHINE DISCOVERY INC., Jiangsu (CN)

(72) Inventors: Jianhua Xia, Shanghai (CN); Zhigan Jiang, Shanghai (CN); Haiying He, Shanghai (CN); Jing Wang, Shanghai (CN)

(73) Assignees: Medshine Discovery, Inc., Jiangsu (CN); Heilongjiang Zhenbaodao Pharmaceutical Co, LTD, Heilongjiang (CN)

( * ) Notice: Subject to any disclaimer, the term of this patent is extended or adjusted under 35 U.S.C. 154(b) by 126 days.

This patent is subject to a terminal disclaimer.

(21) Appl. No.: 16/616,300

(22) PCT Filed: May 24, 2018

(86) PCT No.: PCT/CN2018/088168
§ 371 (c)(1),
(2) Date: Nov. 22, 2019

(87) PCT Pub. No.: WO2018/214929
PCT Pub. Date: Nov. 29, 2018

(65) Prior Publication Data
US 2021/0284630 A1    Sep. 16, 2021

(30) Foreign Application Priority Data

May 24, 2017 (CN) .......................... 201710373576.6

(51) Int. Cl.
*C07D 405/12* (2006.01)
*A61P 11/00* (2006.01)

(52) U.S. Cl.
CPC ............ *C07D 405/12* (2013.01); *A61P 11/00* (2018.01); *C07B 2200/13* (2013.01)

(58) Field of Classification Search
CPC .................................................. C07D 405/12
USPC ......................................................... 546/197
See application file for complete search history.

(56) References Cited

U.S. PATENT DOCUMENTS 10,717,720 B2 * 7/2020 He ...................... C07D 405/12

FOREIGN PATENT DOCUMENTS

| CN | 105367558 A | 3/2016 |
|---|---|---|
| CN | 106800551 A | 6/2017 |
| EP | 3381912 A1 | 10/2018 |
| WO | WO 2016065264 A1 | 4/2016 |
| WO | WO2017/088738 A1 | 6/2017 |

OTHER PUBLICATIONS

Bernstein, "Polymorphism in . . . " p. 115-118, 272 (2002).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Ivanisevic et al. "Use of X-ray . . . " Pharm. Sci. Encycl. p. 1-42 (2010).*
Seddon "Pseudopolymorph . . . " Crystal Growth design v.4(6) p. 1087 (2004) (2 pages from internet).*
Rodriguez-Spong et al., "General principles, etc.," Adv. Drug Delivery Reviews 56 (2004) 241-274.*
Kirk-Othmer Encyclopedia of Chemical Technology, 8, pp. 95-147 (2002).*
Vippagunta et al., "Crystalline Solids", Advanced Drug Delivery Reviews 48 (2001) 3-26.*
Guillory (in Brittain ed.), "Polymorphism in Pharmaceutical Solids.," NY: Marcel Dekker, Inc., 1999, 1-2, 183-226.*
Braga et al., "Making crystals from . . . " J. Royal Soc. Chem. Commun. p. 3635-3645 (2005).*
EP Application No. 18805893.7, Extended European Search Report dated Nov. 28, 2020, 5 pages.
PCT International Search Report for PCT/CN2018/088168 dated Aug. 8, 2018, 4 pages.

* cited by examiner

*Primary Examiner* — Charanjit Aulakh
(74) *Attorney, Agent, or Firm* — Patterson Thuente Pedersen, P.A.

(57) ABSTRACT

The present invention provides a salt and crystal form of a modified andrographolide compound and a preparation method and pharmaceutical use thereof.

(II)

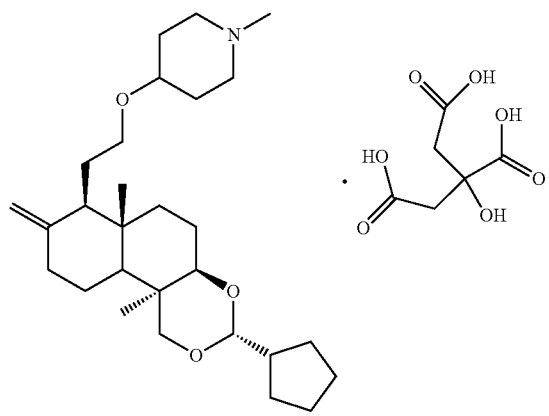

7 Claims, 6 Drawing Sheets

SALT AND CRYSTAL FORM OF MODIFIED ANDROGRAPHOLIDE COMPOUND AND PREPARATION METHOD THEREOF

CROSS REFERENCE TO RELATED PATENT APPLICATIONS

This application is a national phase entry of PCT Application No. PCT/CN2018/088168, filed May 24, 2018, which application claims priority to Chinese Patent Application No. 201710373576.6 filed with China National Intellectual Property Administration on May 24, 2017, the disclosures of which are incorporated herein by reference in their entirety.

TECHNICAL FIELD

The present disclosure relates to a salt form and a crystal form of a modified compound of andrographolide, a preparation method thereof, and a medical use thereof.

BACKGROUND

Idiopathic pulmonary fibrosis (IPF) is a chronic, progressive, irreversible, and lethal fibrotic interstitial pneumonia. "Idiopathic" means that the exact cause of the disease is unknown. Uncertain antigenic stimuli such as smoking and smog cause repeated damage to the lung tissue. The generation of substances such as collagen increases to repair the damaged lung tissue such that the pulmonary interstitium is thickened, thereby making the lung fibrotic and irreversibly lose the function of supplying oxygen to other tissues and organs. In clinical, the disease is mainly characterized by progressive dyspnea caused by hypoxia, dry cough, and gradual decline in lung function, which quickly leads to respiratory failure and death. IPF, also known as a "cancer" that is not exactly a cancer, has characteristics of rapid progression, extremely high disability and mortality, and an average predicted lifetime of 3-5 years after diagnosis. At least 5 million people suffered from the disease in 2008 worldwide. The study in 2015 has shown that the global incidence of IPF reaches 14-59 cases per 100,000, and 30,000-35,000 new cases are confirmed every year. There are about 600,000 patients with idiopathic pulmonary fibrosis in China, and the incidence of IPF has increased significantly in recent years. Due to the lack of an unified and comprehensive IPF diagnostic criteria, many patients have not been diagnosed definitely, so the actual number of patients is far greater than 600,000. The incidence of older people over the age of 75 is 100 times that of people under 35, and 70% of patients are smoking or have a history of smoking. The median survival time of IPF is 2 to 5 years on average, and the 5-year mortality rate is as high as 70%.

SUMMARY

The present disclosure provides a compound of Formula (II).

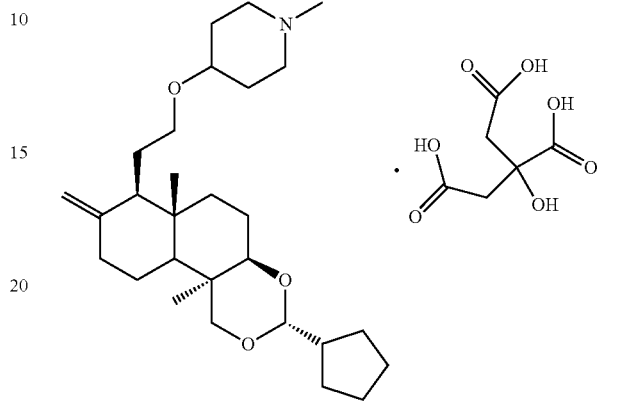

The present disclosure provides Crystal Form A of the compound of Formula (II), which has an X-ray powder diffraction pattern comprising characteristic diffraction peaks at 2θ angles of: 10.00±0.2°, 12.91±0.2°, and 16.27±0.2°.

In some embodiments of the present disclosure, the Crystal Form A has an X-ray powder diffraction pattern comprising characteristic diffraction peaks at 2θ angles of: 5.05±0.2°, 10.00±0.2°, 12.91±0.2°, 13.42±0.2°, 14.51±0.2°, 14.94±0.2°, 16.27±0.2°, and 18.36±0.2°.

In some embodiments of the present disclosure, the Crystal Form A has an XRPD pattern as shown in FIG. 1.

In some embodiments of the present disclosure, the analysis data of the XRPD pattern of the Crystal Form A is as shown in Table 1:

TABLE 1

Analysis data of the XRPD pattern of Crystal Form A of the compound of Formula (II)

| No. | 2θ Angle (°) | Interplanar Spacing (Å) | Peak Area | Relative Intensity (%) |
|---|---|---|---|---|
| 1 | 5.046 | 17.4977 | 174.0 | 25.2 |
| 2 | 7.517 | 11.7507 | 162.4 | 23.5 |
| 3 | 10.007 | 8.8320 | 690.4 | 100.0 |
| 4 | 11.510 | 7.6820 | 74.1 | 10.7 |
| 5 | 12.910 | 6.8515 | 492.1 | 71.3 |
| 6 | 13.425 | 6.5901 | 250.8 | 36.3 |
| 7 | 14.510 | 6.0994 | 342.6 | 49.6 |
| 8 | 14.945 | 5.9229 | 428.2 | 62.0 |
| 9 | 16.271 | 5.4433 | 656.5 | 95.1 |
| 10 | 16.923 | 5.2347 | 111.8 | 16.2 |
| 11 | 17.456 | 5.0761 | 81.4 | 11.8 |
| 12 | 18.364 | 4.8273 | 214.5 | 31.1 |
| 13 | 19.524 | 4.5430 | 63.2 | 9.2 |
| 14 | 19.965 | 4.4435 | 118.9 | 17.2 |
| 15 | 20.774 | 4.2724 | 34.9 | 5.1 |
| 16 | 21.817 | 4.0703 | 85.7 | 12.4 |
| 17 | 22.631 | 3.9258 | 80.1 | 11.6 |
| 18 | 23.142 | 3.8402 | 109.7 | 15.9 |
| 19 | 25.517 | 3.4879 | 45.3 | 6.6 |
| 20 | 26.404 | 3.3727 | 124.0 | 18.0 |

TABLE 1-continued

Analysis data of the XRPD pattern of Crystal
Form A of the compound of Formula (II)

| No. | 2θ Angle (°) | Interplanar Spacing (Å) | Peak Area | Relative Intensity (%) |
|---|---|---|---|---|
| 21 | 26.502 | 3.3604 | 126.8 | 18.4 |
| 22 | 27.019 | 3.2974 | 108.5 | 15.7 |
| 23 | 27.906 | 3.1945 | 46.9 | 6.8 |

In some embodiments of the present disclosure, the Crystal Form A has a differential scanning calorimetry curve comprising endothermic peaks at 119.27° C.±3° C. and 144.42° C.±3° C.

In some embodiments of the present disclosure, the Crystal Form A has a DSC pattern as shown in FIG. 2.

In some embodiments of the present disclosure, the Crystal Form A has a thermogravimetric analysis curve showing a weight loss of 0.1268%±0.1% at 120.00° C.±3° C.

In some embodiments of the present disclosure, the Crystal Form A has a TGA pattern as shown in FIG. 3.

The present disclosure provides a method for preparing the Crystal Form A of the compound of Formula (II), which comprises adding a compound of Formula (II) in any form to an alcoholic organic solvent, and heating and stirring or recrystallizing.

In some embodiments of the present disclosure, the alcoholic solvent is selected from the group consisting of methanol, ethanol, or isopropanol.

In some embodiments of the present disclosure, the stirring is performed at a temperature of from 35° C. to 45° C.

In some embodiments of the present disclosure, the stirring is carried out for 12 hours to 36 hours.

In some embodiments of the present disclosure, the weight ratio of the compound of Formula (II) to the alcoholic organic solvent is from 1:1 to 1:3.

The present disclosure further provides use of the compound of Formula (II) or the Crystal Form A for the preparation of a medicament for the treatment of idiopathic pulmonary fibrosis, respiratory infection, or pneumonia.

The present disclosure further provides use of Compound h for the preparation of a medicament for the treatment of idiopathic pulmonary fibrosis, respiratory infection, or pneumonia.

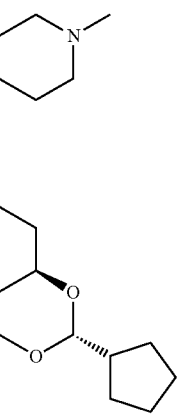

h

Definitions and Illustrations

Unless otherwise stated, the following terms and phrases as used herein are intended to have the following meanings.

A specific phrase or term should not be considered as indefinite or unclear if it is not particularly defined, but should be understood as its ordinary meaning. When a trade name appears herein, it is intended to refer to its corresponding commodity or its active ingredient.

The intermediate compounds in the present disclosure can be prepared by a variety of synthetic methods well-known to those skilled in the art, including the specific embodiments listed below, combinations thereof with other chemical synthesis methods, and equivalents well-known to those skilled in the art. Preferred embodiments include, but are not limited to, Examples in the present disclosure.

The chemical reactions of specific embodiments in the present disclosure were carried out in suitable solvents. It is required that the solvents are suitable for the chemical changes of the present disclosure and the reagents and materials required therefor. In order to obtain the compound of the present disclosure, it is sometimes necessary for those skilled in the art to modify or select synthetic steps or reaction schemes based on the existing embodiments.

The present disclosure will be specifically described by the following examples, which are not intended to limit the present disclosure.

All solvents used in the present disclosure are commercially available and can be used without further purification.

The following abbreviations are used in the present disclosure: r.t. represents room temperature; THF represents tetrahydrofuran; NMP represents N-methylpyrrolidone; $MeSO_3H$ represents methanesulfonic acid; DME represents dimethoxyethane; DCM represents dichloromethane; Xphos represents 2-bicyclohexylphosphine-2'4'6'-triisopropylbiphenyl; EtOAc represents ethyl acetate; MeOH represents methanol; acetone represents acetone; 2-Me-THF represents 2-methyltetrahydrofuran; IPA represents isopropanol.

Compounds are named manually or by ChemDraw®, and commercial compounds use product names under the supplier's catalogue.

X-Ray Powder Diffraction (XRPD) in the Present Disclosure

Instrument model: Bruker D8 advance X-ray diffractometer

Testing method: About 10-20 mg of a sample is used for XRPD detection.

Detailed XRPD parameters:
Light pipe: Cu, kα, (λ=1.54056Å).
Voltage of light pipe: 40 kV, light pipe current: 40 mA
Divergence slit: 0.60 mm
Detector slit: 10.50 mm
Anti-scattering slit: 7.10 mm
Scan range: 4-40 deg
Step size: 0.02 deg
Step length: 0.12 seconds
Rotation speed of sample pan: 15 rpm Differential Scanning Calorimetry (DSC) in the Present Disclosure Instrument model: TA Q2000 differential scanning calorimeter Testing method: A sample (~1 mg) is taken and placed in a DSC aluminum pan for testing. The sample is heated from 30° C. (room temperature) to 300° C. (or 350° C.) at a heating rate of 10° C./min under the condition of 50 mL/min $N_2$.

Thermal Gravimetric Analysis (TGA) in the Present Disclosure

Instrument model: TA Q5000IR thermal gravimetric analyzer

Testing method: A sample (2 to 5 mg) is taken and placed in a TGA platinum pan for testing. The sample is heated from room temperature at a heating rate of 10° C./min under the condition of 25 mL/min $N_2$. The endpoint is set at 300° C. or at a weight loss of 20%.

Technical Effects

The crystal form of the compound of Formula (II) as mentioned in the present disclosure has good stability and is easy to be prepared into a medicine. In addition, it has an obvious inhibitory effect on cytokines involved in the IPF-related pathway. The compound of Formula (II) has a significant inhibitory effect on IPF as shown in a SD rat model of left unilateral pulmonary fibrosis.

DETAILED DESCRIPTION

Figure 1:
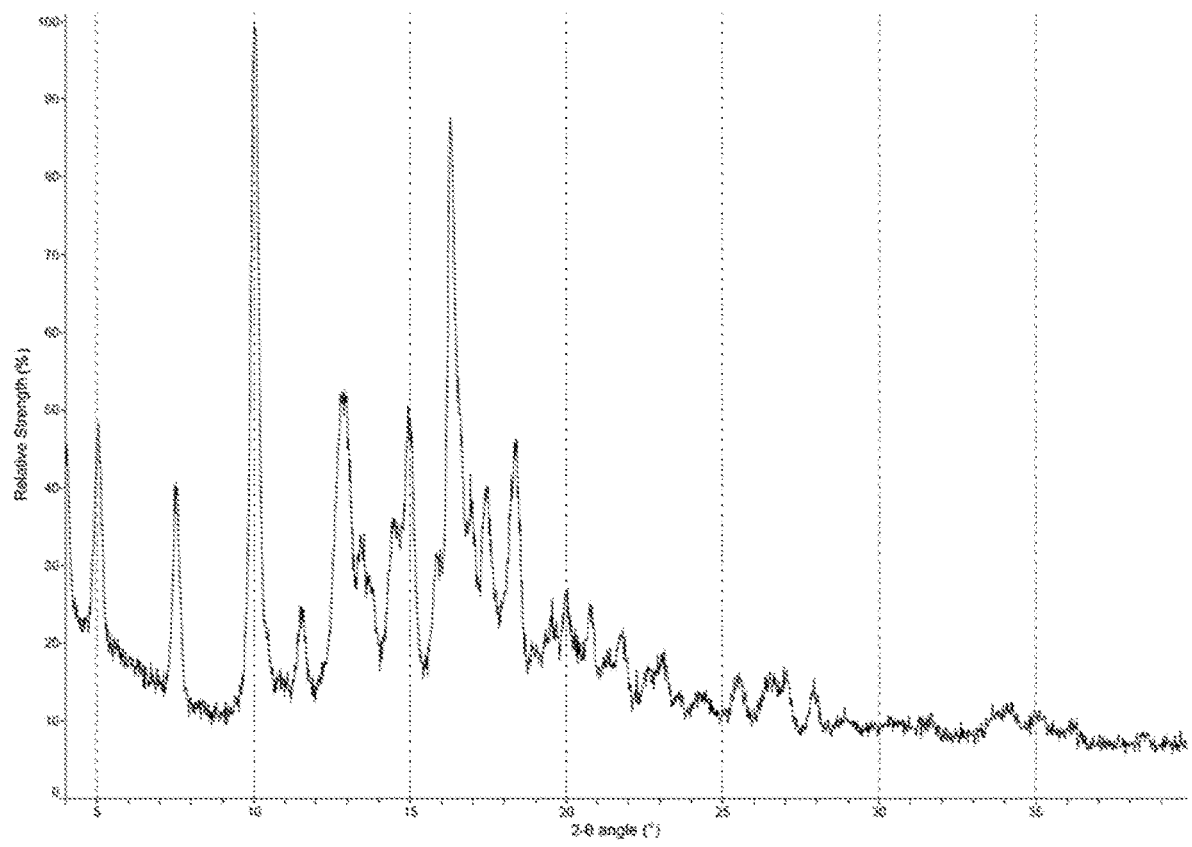
FIG. 1 shows the XRPD spectrum of Cu-Kα radiation of Crystal Form A of the compound of Formula (II)

In order to better understand the content of the present disclosure, the present disclosure will be further described below in conjunction with specific examples. However, the specific embodiments are not intended to limit the content of the present disclosure.

Example 1: Preparation of the Compound of Formula (II)

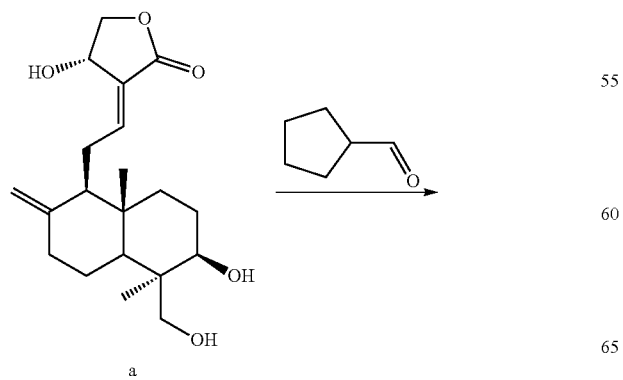

a

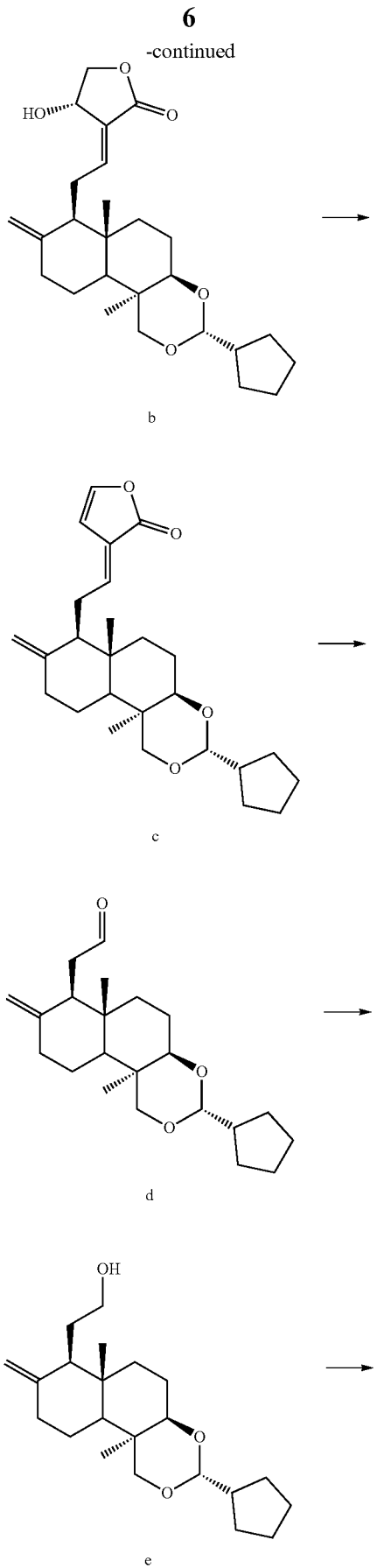

b c d e

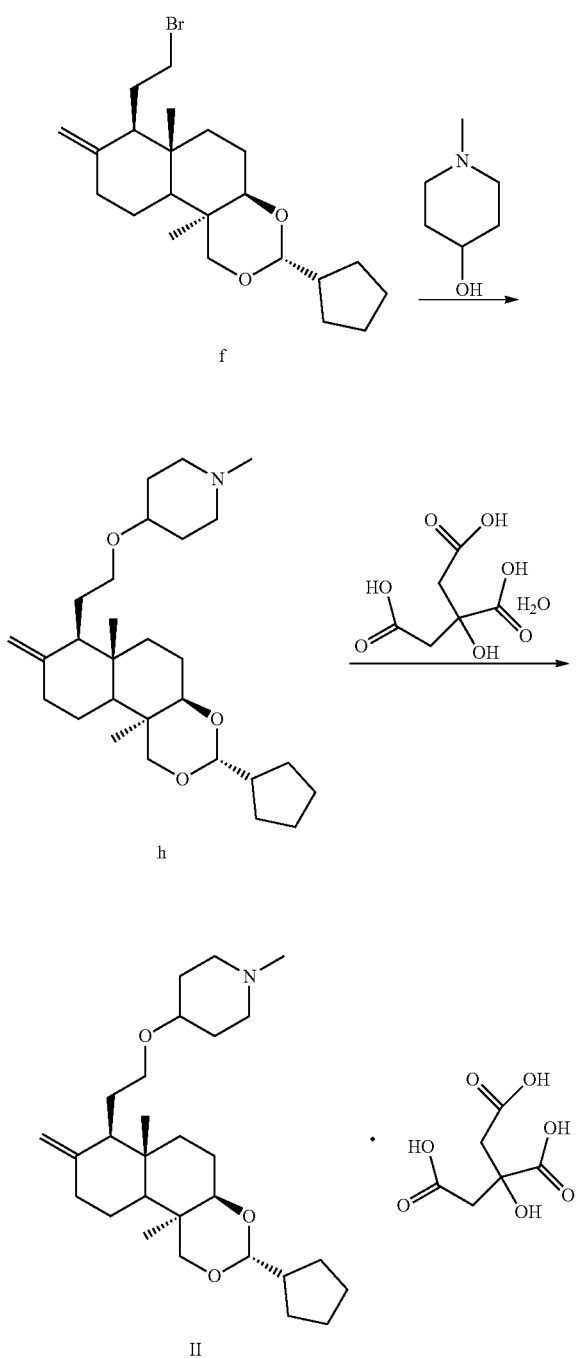

4.29-4.26 (m, 1H), 4.03 (d, J=10.8 Hz, 1H), 3.49-3.44 (m, 2H), 2.59-2.46 (m, 4H), 2.21 (s, 1H), 2.08-1.87 (m, 2H), 1.85-1.71 (m, 3H), 1.69-1.56 (m, 9H), 1.54 (s, 3H), 1.52-1.26 (m, 3H), 0.83 (s, 3H).

Step 2: Preparation of Compound c

Compound b (200.00 g, 464.49 mmol) was dissolved in 2000 mL of dichloromethane, and acetic anhydride (490.50 g, 4.80 mol) and pyridine (392.00 g, 4.96 mol) were added thereto at 0° C. The mixture was then stirred at 20° C. for 17 hours. The reaction solution was concentrated under reduced pressure at 35° C., then 6000 mL of water was added thereto, and precipitates were formed. The residue obtained after filtration was homogenated with petroleum ether (500 mL*2) to obtain 200 g of Compound c as a crude product.

$^1$H NMR (400 MHz, CDCl$_3$) □□7.02 (br. s., 1H), 6.71 (t, J=6.9 Hz, 1H), 6.19 (d, J=3.0 Hz, 1H), 4.88 (s, 1H), 4.62 (d, J=5.5 Hz, 1H), 4.45 (s, 1H), 4.04 (d, J=11.3 Hz, 1H), 3.55-3.36 (m, 2H), 2.63-2.52 (m, 1H), 2.48-2.38 (m, 2H), 2.35-2.23 (m, 1H), 2.15-1.99 (m, 2H), 1.94-1.82 (m, 3H), 1.72 (br. s., 3H), 1.64-1.45 (m, 6H), 1.39 (s, 3H), 1.27 (br. s., 3H), 0.83 (s, 3H).

Step 3: Preparation of Compound d

Compound c (200.00 g, 484.78 mmol) was dissolved in 2000 mL of tetrahydrofuran, and a solution of potassium permanganate (229.83 g, 1.45 mol) dissolved in 2000 mL of water was added thereto at 0° C. The mixture was then stirred at 20° C. for 6 hours. 1000 mL of brine was added, and layers were separated. The organic phase was concentrated under reduced pressure. The obtained residue was dissolved in ethyl acetate (1000 mL), 9000 mL of petroleum ether was added thereto, and the mixture was filtered. The filtrate was concentrated under reduced pressure to give 78 g of Compound d as a crude product.

$^1$H NMR (400 MHz, CDCl$_3$) □□9.65 (d, J=2.0 Hz, 1H), 4.85 (s, 1H), 4.60 (d, J=6.0 Hz, 1H), 4.43 (s, 1H), 4.03 (d, J=11.0 Hz, 1H), 3.53-3.42 (m, 2H), 2.55-2.21 (m, 5H), 2.14-2.06 (m, 2H), 1.86-1.80 (m, 1H), 1.72-1.67 (m, 3H), 1.61-1.43 (m, 7H), 1.38 (s, 3H), 1.26-1.09 (m, 3H), 0.83-0.66 (m, 3H).

Step 4: Preparation of Compound e

Compound d (70.00 g, 202.02 mmol) was dissolved in 1000 mL of tetrahydrofuran, and sodium borohydride (22.93 g, 606.06 mmol) was added thereto at 0° C. The mixture was then stirred at 25° C. for 4 hours, quenched with 500 mL of water, and extracted with ethyl acetate (200 mL*5). The organic phase was combined, washed with a saturated sodium chloride solution (200 mL*1), dried over anhydrous sodium sulfate, and filtered. The filtrate was concentrated under reduced pressure. The obtained residue was purified by silica gel column chromatography with a eluent system of PE:EA=10:1 to 2:1 to give Compound e (40 g, yield: 56.8%).

$^1$H NMR (400 MHz, CDCl$_3$) □□4.87 (s, 1H), 4.61 (d, J=6 Hz, 2H), 4.03 (d, J=11.2 Hz, 1H), 3.75 (s, 1H), 3.52-3.43 (m, 3H), 2.44-2.41 (m, 2H), 2.08-1.75 (m, 3H), 1.74-1.66 (m, 7H), 1.57-1.54 (m, 6H), 1.37 (s, 4H), 1.26-1.25 (m, 3H), 0.77 (s, 3H).

Step 1: Preparation of Compound b

Compound a (300.00 g, 856.04 mmol) was dissolved in dichloromethane (3.00 L), and cyclopentylcarbaldehyde (84.85 g, 864.60 mmol) and ion exchange resin-15 (300.00 g) were added sequentially thereto. The mixture was stirred at 20° C. for 12 hours. The system was concentrated by filtration to give Compound b as a white solid (300 g, yield: 81.39%).

$^1$H NMR (400 MHz, CDCl3) □□6.97 (d, J=6.4 Hz, 1H), 5.05 (s, 1H), 4.92 (s, 1H), 4.62 (s, 2H), 4.46 (d, J=6 Hz, 1H),

Step 5: Preparation of Compound f

Compound e (35.00 g, 100.42 mmol) was dissolved in 500 mL of dichloromethane, and carbon tetrabromide (36.63 g, 110.46 mmol) and triphenylphosphine (28.97 g, 110.46 mmol) were added thereto at 25° C. The mixture was stirred at 25° C. for 4 hours, quenched with water (200 mL), and extracted with dichloromethane (200 mL*3). The organic phase was combined, washed with a saturated sodium chloride solution (200 mL*1), dried over anhydrous sodium sulfate, and filtered. The filtrate was concentrated under reduced pressure. The obtained residue was purified by silica gel column chromatography with a eluent system of PE:EtOAc=10:1 to 5:1 to give Compound f (40 g, yield: 96.82%).

$^1$H NMR (400 MHz, CDCl$_3$) □□4.89 (s, 1H), 4.61 (d, J=6 Hz, 1H), 4.53 (s, 1H), 4.02 (d, J=11.2 Hz, 1H), 3.55-3.52 (m, 3H), 3.46-3.29 (m, 1H), 2.42 (s, 1H), 2.08 (s, 1H), 2.04-1.84 (m, 4H), 1.84-1.81 (m, 3H), 1.72-1.70 (m, 3H), 1.59-1.54 (m, 6H), 1.38 (s, 3H), 1.26-1.22 (m, 3H), 0.78 (s, 3H).

Step 6: Preparation of Compound h 1-methylpiperidin-4-ol 276 g (84 mg, 0.73 mmol) was dissolved in N,N-dimethylformamide (10 mL), and sodium hydrogen (32 mg, 1.01 mmol) was added thereto at 0° C. and the mixture was stirred at 0° C. for 15 minutes. Compound f (300 mg, 0.73 mmol) was added to the reaction solution and the mixture was stirred at room temperature for 12 hours. Water (5 mL) was added to the reaction solution. The mixture was extracted with ethyl acetate (30 mL). The organic phase was washed with water (10 mL*3), dried over anhydrous sodium sulfate, and filtered. The filtrate was concentrated under reduced pressure followed by isolation through preparative liquid chromatography to give Compound h (20 mg, yield: 6.1%).

MS m/z (ESI): 446.6 [M+1]

$^1$H NMR (400 MHz, CDCl$_3$) □□8.44-8.55 (m, 1H), 4.54-4.66 (m, 4H), 4.02-4.07 (m, 1H), 3.40-3.53 (m, 3H), 2.96-3.16 (m, 3H), 2.77-2.92 (m, 2H), 2.56-2.65 (m, 3H), 2.25-2.40 (m, 2H), 1.45-2.03 (m, 19H), 1.30 (s, 3H), 1.15-1.26 (m, 3H), 0.76 (s, 3H).

Step 7: Preparation of the Compound of Formula (II)

Compound h (1.55 kg, 3.28 mol) was dissolved in acetone (15.5 L). The solution was then added to a 30 L reactor with the temperature being controlled at 22° C. A solution of aqueous citric acid (550.5 g, 2.62 mol) in acetone (7.8 L) was added. The reaction was stirred at 22° C. for 17.7 h, and then a large amount of solids were precipitated in the reaction solution. The mixture was filtered under nitrogen. The filter cake was washed with acetone (5.0 L*4), and filtered again. The filter cake was added to a 30 L reactor at 22° C., and then acetone (15.5 L) was added thereto. The reaction solution was stirred at 22° C. for additional 21.4 h, and then filtered under nitrogen. The filter cake was dried in a vacuum oven at 40° C. for 48 h to obtain the compound of Formula (II) as a crude off-white solid (1.3067 kg).

Example 2: Preparation of Crystal Form A

The compound of Formula (II) as a crude off-white solid (1091.8 g, 1.96 mol) was added to a 5 L flask with the temperature being controlled at 40° C., and then MeOH (3037 mL) was added thereto. After the addition, the reaction was stirred at 40° C. for 24 h. The reaction solution was filtered while hot. The filter cake was washed with MeOH (200 mL) and then filtered to give a crude product. The crude product was dried in a vacuum oven to give Crystal Form A as a fine white solid (869.34 g).

Example 3: Preparation of the Compound of Formula (III)

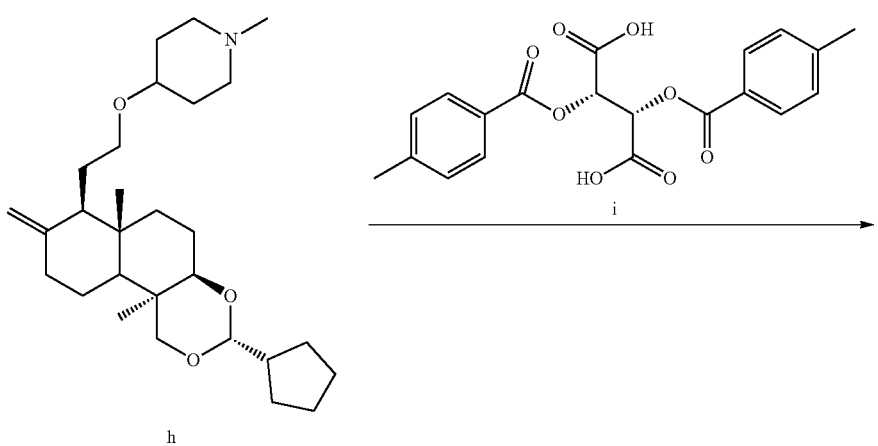

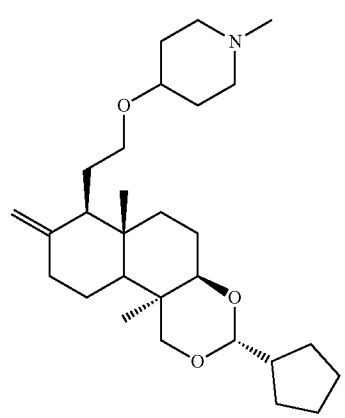

-continued

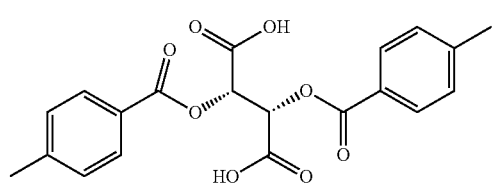

III

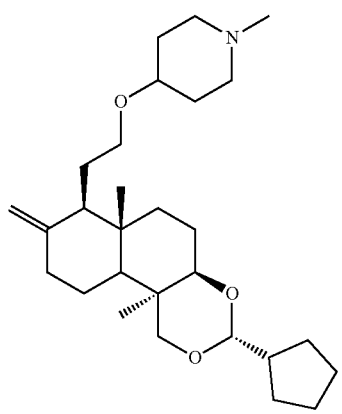

The Compound h (1.0 g, 2.24 mmol) was dissolved in acetone (10 mL), and a solution of i (1.3 g, 3.36 mmol) in acetone (5 mL) was added thereto at 15° C. After the addition, the reaction was stirred at 15° C. for additional 1 h and then filtered. The filter cake was washed with acetone (20 mL) and filtered again. The filter cake was dried in a vacuum oven to give the compound of Formula (III) as a white solid (0.92 g).

A single crystal of the compound of Formula (III) was incubated in a mixed solvent of dichloromethane and methanol (volume ratio of dichloromethane:methanol=3:7), and was confirmed to have the absolute configuration as shown in Formula (III-1).

-continued

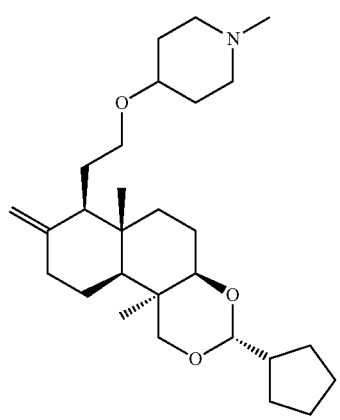

According to the configuration of the compound of Formula (III-1), the compound of Formula (II) was speculated to have the absolute configuration as shown in Formula (II-1).

III-1

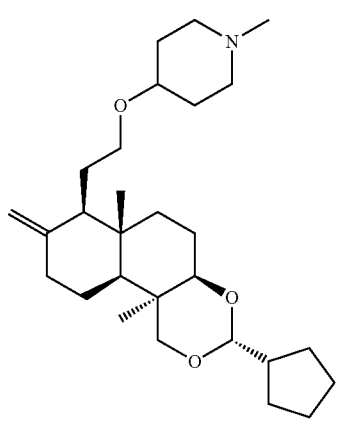

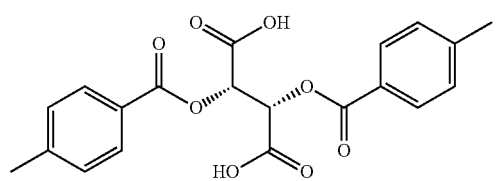

(II-1)

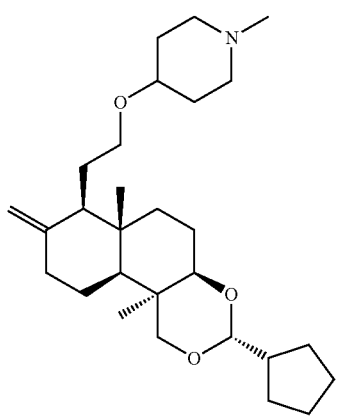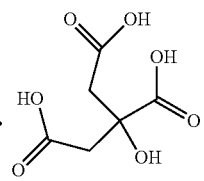

The single crystal data of the compound of Formula (III-1) were as follows.

Refinement Information on the Crystal Structure of the Compound of Formula (III-1)

| | |
|---|---|
| Identification code | 499 |
| Empirical Formula | C77 H114 Cl2 N2 O14 |
| Formula weight | 1362.60 |
| Temperature | 296(2) K |
| Wavelength | 1.54178 A |
| Crystal system, space group | Monoclinic, C 2 |
| Unit cell dimensions | a = 18.493(3) A alpha = 90 deg. |
| | b = 7.5421(10) A beta = 90.035(9) deg |
| | c = 27.647(4) A gamma = 90 deg. |
| Volume | 3856.2(9) A^3 |
| Z, Calculated density | 2, 1.174 Mg/m^3 |
| Absorption coefficient | 1.249 mm^−1 |
| F(000) | 1472 |
| Crystal size | 0.30 × 0.20 × 0.02 mm |
| Theta range for data collection | 1.60 to 66.98 deg. |
| Limiting indices | −21 <= h <= 19, −8 <= k <= 8, −32 <= l <= 32 |
| Reflections collected/unique | 12186/6166 [R(int) = 0.0664] |
| Completeness to theta = 66.98 | 97.7% |
| Absorption correction | Semi-empirical from equivalents |
| Max. and min. transmission | 0.7533 and 0.4630 |
| Refinement method | Full-matrix least-squares on F^2 |
| Data/restraints/parameters | 6166/1/429 |
| Goodness-of-fit on F^2 | 1.054 |
| Final R indices [I > 2sigma(I)] | R1 = 0.0866, wR2 = 0.2357 |
| R indices (all data) | R1 = 0.1009, wR2 = 0.2518 |
| Absolute structure parameter | 0.04(6) |
| Largest diff. peak and hole | 0.576 and −0.521 e · A^−3 |

Atomic Coordinate Parameters and Equivalent Temperature Factor Values of the Compound of Formula (III-1)

| | x | y | z | U(eq) |
|---|---|---|---|---|
| Cl(1) | 4398(2) | −2648(5) | −308(2) | 211(2) |
| O(1) | 7711(2) | 7945(5) | 3172(1) | 62(1) |
| O(2) | 4311(2) | 2671(5) | 1486(1) | 51(1) |
| O(3) | 4949(2) | 1703(5) | 804(1) | 52(1) |
| O(4) | 9022(2) | 10735(5) | 6039(1) | 66(1) |
| O(5) | 9803(2) | 9807(4) | 5464(1) | 45(1) |
| O(6) | 8570(2) | 9981(5) | 4948(1) | 55(1) |
| O(7) | 8820(2) | 12677(5) | 4668(2) | 56(1) |
| N(1) | 7493(2) | 10136(6) | 4316(2) | 54(1) |
| C(1) | 7082(3) | 4389(6) | 2329(2) | 47(1) |
| C(1') | 5000 | −1467(15) | 0 | 117(4) |
| C(2) | 7751(3) | 3360(8) | 2154(2) | 59(1) |
| C(3) | 7581(3) | 1444(8) | 2047(2) | 64(2) |
| C(4) | 6948(3) | 1280(6) | 1681(2) | 54(1) |
| C(5) | 6288(2) | 2317(5) | 1856(2) | 39(1) |
| C(6) | 5586(2) | 1847(5) | 1578(2) | 40(1) |
| C(7) | 4957(3) | 2986(6) | 1765(2) | 44(1) |
| C(8) | 5134(3) | 4951(6) | 1803(2) | 53(1) |
| C(9) | 5792(3) | 5225(6) | 2124(2) | 48(1) |
| C(10) | 6459(2) | 4311(5) | 1932(2) | 40(1) |
| C(11) | 7261(3) | 6255(7) | 2519(2) | 58(1) |
| C(12) | 7602(4) | 6233(8) | 3003(2) | 77(2) |
| C(13) | 8211(3) | 8071(8) | 3563(2) | 63(1) |
| C(14) | 8358(4) | 10011(9) | 3643(2) | 77(2) |
| C(15) | 7713(4) | 10987(8) | 3854(2) | 71(2) |
| C(16) | 7305(3) | 8230(8) | 4229(2) | 60(1) |
| C(17) | 7944(3) | 7274(8) | 4023(2) | 66(2) |
| C(18) | 6875(4) | 11039(12) | 4559(3) | 107(3) |
| C(19) | 8385(4) | 4022(11) | 2067(3) | 92(2) |
| C(20) | 6733(3) | 5269(7) | 1471(2) | 57(1) |
| C(21) | 5403(3) | −107(7) | 1679(2) | 63(1) |
| C(22) | 5636(3) | 2076(7) | 1031(2) | 50(1) |
| C(23) | 4409(3) | 2858(6) | 979(2) | 48(1) |
| C(24) | 3705(3) | 2436(7) | 742(2) | 55(1) |
| C(25) | 3720(3) | 2553(9) | 194(2) | 71(2) |
| C(26) | 3026(4) | 3516(12) | 37(3) | 89(2) |
| C(27) | 2584(4) | 3641(14) | 488(3) | 109(3) |
| C(28) | 3090(3) | 3643(9) | 896(2) | 71(2) |
| C(29) | 9892(3) | 4714(7) | 6585(2) | 57(1) |
| C(30) | 9443(4) | 5953(9) | 6788(2) | 74(2) |
| C(31) | 9304(3) | 7528(8) | 6564(2) | 59(1) |
| C(32) | 9608(2) | 7916(6) | 6112(2) | 38(1) |
| C(33) | 10044(2) | 6655(6) | 5903(2) | 43(1) |
| C(34) | 10192(3) | 5063(7) | 6133(2) | 48(1) |
| C(35) | 9434(2) | 9623(6) | 5883(2) | 41(1) |
| C(36) | 9679(2) | 11372(6) | 5180(2) | 37(1) |
| C(37) | 8960(2) | 11343(7) | 4902(2) | 42(1) |
| C(38) | 10060(5) | 2984(9) | 6838(3) | 88(2) |
| H(1A) | 7878 | 10170 | 4520 | 64 |
| H(1B) | 6898 | 3728 | 2608 | 56 |
| H(3A) | 7453 | 844 | 2346 | 77 |
| H(3B) | 8007 | 869 | 1916 | 77 |
| H(4A) | 7100 | 1731 | 1369 | 64 |
| H(4B) | 6820 | 41 | 1642 | 64 |
| H(5A) | 6203 | 1867 | 2183 | 47 |
| H(7A) | 4855 | 2577 | 2094 | 53 |
| H(8A) | 5230 | 5425 | 1483 | 64 |
| H(8B) | 4723 | 5582 | 1937 | 64 |
| H(9A) | 5888 | 6486 | 2152 | 58 |
| H(9B) | 5687 | 4776 | 2445 | 58 |
| H(11A) | 7585 | 6835 | 2293 | 69 |
| H(11B) | 6820 | 6947 | 2534 | 69 |
| H(12A) | 7294 | 5593 | 3227 | 92 |
| H(12B) | 8062 | 5620 | 2985 | 92 |
| H(13A) | 8663 | 7483 | 3471 | 75 |
| H(14A) | 8487 | 10552 | 3336 | 93 |
| H(14B) | 8767 | 10137 | 3859 | 93 |
| H(15A) | 7840 | 12217 | 3912 | 86 |
| H(15B) | 7313 | 10958 | 3627 | 86 |
| H(16A) | 7163 | 7679 | 4532 | 72 |
| H(16B) | 6901 | 8153 | 4007 | 72 |
| H(17A) | 7812 | 6048 | 3964 | 79 |
| H(17B) | 8332 | 7281 | 4259 | 79 |
| H(18A) | 6767 | 10442 | 4857 | 160 |
| H(18B) | 6459 | 11006 | 4351 | 160 |
| H(18C) | 7002 | 12249 | 4625 | 160 |
| H(19A) | 8747 | 3311 | 1937 | 110 |
| H(19B) | 8478 | 5208 | 2135 | 110 |
| H(20A) | 6829 | 6490 | 1545 | 85 |
| H(20B) | 6370 | 5201 | 1223 | 85 |
| H(20C) | 7168 | 4711 | 1360 | 85 |
| H(21A) | 5786 | −849 | 1562 | 94 |
| H(21B) | 4960 | −412 | 1518 | 94 |
| H(21C) | 5347 | −280 | 2021 | 94 |
| H(22A) | 5780 | 3282 | 957 | 60 |
| H(22B) | 6001 | 1281 | 904 | 60 |
| H(23A) | 4543 | 4086 | 906 | 57 |
| H(24A) | 3574 | 1219 | 830 | 66 |
| H(25A) | 3737 | 1375 | 54 | 85 |
| H(25B) | 4142 | 3208 | 88 | 85 |
| H(26A) | 3135 | 4686 | −89 | 107 |
| H(26B) | 2772 | 2845 | −210 | 107 |
| H(27A) | 2300 | 4722 | 487 | 131 |
| H(27B) | 2257 | 2638 | 512 | 131 |
| H(28A) | 2859 | 3194 | 1186 | 86 |
| H(28B) | 3266 | 4833 | 959 | 86 |
| H(30A) | 9229 | 5714 | 7085 | 89 |
| H(31A) | 9004 | 8353 | 6713 | 71 |
| H(33A) | 10245 | 6875 | 5600 | 51 |
| H(34A) | 10490 | 4229 | 5986 | 57 |
| H(36A) | 9702 | 12426 | 5387 | 44 |
| H(38A) | 10381 | 2291 | 6641 | 132 |
| H(38B) | 9620 | 2338 | 6890 | 132 |
| H(38C) | 10286 | 3225 | 7144 | 132 |

The Bond Lengths and Bond Angles of Bonded Atoms in the Compound of Formula (III-1)

| | |
|---|---|
| Cl(1)—C(1') | 1.660(7) |
| O(1)—C(12) | 1.388(7) |
| O(1)—C(13) | 1.426(6) |
| O(2)—C(23) | 1.419(5) |
| O(2)—C(7) | 1.442(6) |
| O(3)—C(23) | 1.413(6) |
| O(3)—C(22) | 1.444(6) |
| O(4)—C(35) | 1.212(6) |
| O(5)—C(35) | 1.351(5) |
| O(5)—C(36) | 1.436(5) |
| O(6)—C(37) | 1.261(6) |
| O(7)—C(37) | 1.224(6) |
| N(1)—C(15) | 1.484(8) |
| N(1)—C(18) | 1.490(7) |
| N(1)—C(16) | 1.498(7) |
| N(1)—H(1A) | 0.9100 |
| C(1)—C(2) | 1.539(7) |
| C(1)—C(11) | 1.539(6) |
| C(1)—C(10) | 1.593(6) |
| C(1)—H(1B) | 0.9800 |
| C(1')—Cl(1)#1 | 1.660(7) |
| C(2)—C(19) | 1.298(8) |
| C(2)—C(3) | 1.508(8) |
| C(3)—C(4) | 1.551(7) |
| C(3)—H(3A) | 0.9700 |
| C(3)—H(3B) | 0.9700 |
| C(4)—C(5) | 1.528(6) |
| C(4)—H(4A) | 0.9700 |
| C(4)—H(4B) | 0.9700 |
| C(5)—C(10) | 1.551(6) |
| C(5)—C(6) | 1.550(6) |
| C(5)—H(5A) | 0.9800 |
| C(6)—C(22) | 1.523(6) |
| C(6)—C(7) | 1.536(6) |
| C(6)—C(21) | 1.539(6) |
| C(7)—C(8) | 1.521(7) |
| C(7)—H(7A) | 0.9800 |
| C(8)—C(9) | 1.520(7) |
| C(8)—H(8A) | 0.9700 |
| C(8)—H(8B) | 0.9700 |
| C(9)—C(10) | 1.510(6) |
| C(9)—H(9A) | 0.9700 |
| C(9)—H(9B) | 0.9700 |
| C(10)—C(20) | 1.550(7) |
| C(11)—C(12) | 1.478(7) |
| C(11)—H(11A) | 0.9700 |
| C(11)—H(11B) | 0.9700 |
| C(12)—H(12A) | 0.9700 |
| C(12)—H(12B) | 0.9700 |
| C(13)—C(17) | 1.489(9) |
| C(13)—C(14) | 1.504(9) |
| C(13)—H(13A) | 0.9800 |
| C(14)—C(15) | 1.520(9) |
| C(14)—H(14A) | 0.9700 |
| C(14)—H(14B) | 0.9700 |
| C(15)—H(15A) | 0.9700 |
| C(15)—H(15B) | 0.9700 |
| C(16)—C(17) | 1.497(8) |
| C(16)—H(16A) | 0.9700 |
| C(16)—H(16B) | 0.9700 |
| C(17)—H(17A) | 0.9700 |
| C(17)—H(17B) | 0.9700 |
| C(18)—H(18A) | 0.9600 |
| C(18)—H(18B) | 0.9600 |
| C(18)—H(18C) | 0.9600 |
| C(19)—H(19A) | 0.9300 |
| C(19)—H(19B) | 0.9300 |
| C(20)—H(20A) | 0.9600 |
| C(20)—H(20B) | 0.9600 |
| C(20)—H(20C) | 0.9600 |
| C(21)—H(21A) | 0.9600 |
| C(21)—H(21B) | 0.9600 |
| C(21)—H(21C) | 0.9600 |
| C(22)—H(22A) | 0.9700 |
| C(22)—H(22B) | 0.9700 |
| C(23)—C(24) | 1.492(7) |
| C(23)—H(23A) | 0.9800 |
| C(24)—C(28) | 1.518(7) |
| C(24)—C(25) | 1.517(8) |
| C(24)—H(24A) | 0.9800 |
| C(25)—C(26) | 1.538(9) |
| C(25)—H(25A) | 0.9700 |
| C(25)—H(25B) | 0.9700 |
| C(26)—C(27) | 1.495(10) |
| C(26)—H(26A) | 0.9700 |
| C(26)—H(26B) | 0.9700 |
| C(27)—C(28) | 1.465(9) |
| C(27)—H(27A) | 0.9700 |
| C(27)—H(27B) | 0.9700 |
| C(28)—H(28A) | 0.9700 |
| C(28)—H(28B) | 0.9700 |
| C(29)—C(30) | 1.370(8) |
| C(29)—C(34) | 1.391(7) |
| C(29)—C(38) | 1.514(8) |
| C(30)—C(31) | 1.364(8) |
| C(30)—H(30A) | 0.9300 |
| C(31)—C(32) | 1.403(6) |
| C(31)—H(31A) | 0.9300 |
| C(32)—C(33) | 1.375(6) |
| C(32)—C(35) | 1.470(6) |
| C(33)—C(34) | 1.386(7) |
| C(33)—H(33A) | 0.9300 |
| C(34)—H(34A) | 0.9300 |
| C(36)—C(37) | 1.535(5) |
| C(36)—C(36)#2 | 1.553(8) |
| C(36)—H(36A) | 0.9800 |
| C(38)—H(38A) | 0.9600 |
| C(38)—H(38B) | 0.9600 |
| C(38)—H(38C) | 0.9600 |
| C(12)—O(1)—C(13) | 114.3(4) |
| C(23)—O(2)—C(7) | 113.9(3) |
| C(23)—O(3)—C(22) | 110.6(3) |
| C(35)—O(5)—C(36) | 118.1(3) |
| C(15)—N(1)—C(18) | 113.6(5) |
| C(15)—N(1)—C(16) | 110.0(4) |
| C(18)—N(1)—C(16) | 109.4(5) |
| C(15)—N(1)—H(1A) | 107.9 |
| C(18)—N(1)—H(1A) | 107.9 |
| C(16)—N(1)—H(1A) | 107.9 |
| C(2)—C(1)—C(11) | 113.3(4) |
| C(2)—C(1)—C(10) | 110.2(4) |
| C(11)—C(1)—C(10) | 115.2(4) |
| C(2)—C(1)—H(1B) | 105.8 |
| C(11)—C(1)—H(1B) | 105.8 |
| C(10)—C(1)—H(1B) | 105.8 |
| Cl(1)—C(1')—Cl(1)#1 | 115.1(7) |
| C(19)—C(2)—C(3) | 121.4(6) |
| C(19)—C(2)—C(1) | 126.2(6) |
| C(3)—C(2)—C(1) | 112.2(5) |
| C(2)—C(3)—C(4) | 111.1(4) |
| C(2)—C(3)—H(3A) | 109.4 |
| C(4)—C(3)—H(3A) | 109.4 |
| C(2)—C(3)—H(3B) | 109.4 |
| C(4)—C(3)—H(3B) | 109.4 |
| H(3A)—C(3)—H(3B) | 108.0 |
| C(5)—C(4)—C(3) | 110.8(4) |
| C(5)—C(4)—H(4A) | 109.5 |
| C(3)—C(4)—H(4A) | 109.5 |
| C(5)—C(4)—H(4B) | 109.5 |
| C(3)—C(4)—H(4B) | 109.5 |
| H(4A)—C(4)—H(4B) | 108.1 |
| C(4)—C(5)—C(10) | 112.2(4) |
| C(4)—C(5)—C(6) | 113.3(4) |
| C(10)—C(5)—C(6) | 117.3(3) |
| C(4)—C(5)—H(5A) | 104.1 |
| C(10)—C(5)—H(5A) | 104.1 |
| C(6)—C(5)—H(5A) | 104.1 |
| C(22)—C(6)—C(7) | 108.5(4) |
| C(22)—C(6)—C(21) | 107.6(4) |
| C(7)—C(6)—C(21) | 107.9(4) |
| C(22)—C(6)—C(5) | 114.6(4) |
| C(7)—C(6)—C(5) | 109.8(3) |
| C(21)—C(6)—C(5) | 108.3(4) |
| O(2)—C(7)—C(8) | 112.0(4) |
| O(2)—C(7)—C(6) | 110.8(4) |

-continued

| | |
|---|---|
| C(8)—C(7)—C(6) | 113.9(4) |
| O(2)—C(7)—H(7A) | 106.5 |
| C(8)—C(7)—H(7A) | 106.5 |
| C(6)—C(7)—H(7A) | 106.5 |
| C(9)—C(8)—C(7) | 110.2(4) |
| C(9)—C(8)—H(8A) | 109.6 |
| C(7)—C(8)—H(8A) | 109.6 |
| C(9)—C(8)—H(8B) | 109.6 |
| C(7)—C(8)—H(8B) | 109.6 |
| H(8A)—C(8)—H(8B) | 108.1 |
| C(10)—C(9)—C(8) | 112.7(4) |
| C(10)—C(9)—H(9A) | 109.1 |
| C(8)—C(9)—H(9A) | 109.0 |
| C(10)—C(9)—H(9B) | 109.1 |
| C(8)—C(9)—H(9B) | 109.1 |
| H(9A)—C(9)—H(9B) | 107.8 |
| C(9)—C(10)—C(5) | 109.0(4) |
| C(9)—C(10)—C(20) | 110.1(4) |
| C(5)—C(10)—C(20) | 114.1(4) |
| C(9)—C(10)—C(1) | 109.4(4) |
| C(5)—C(10)—C(1) | 106.0(3) |
| C(20)—C(10)—C(1) | 108.2(4) |
| C(12)—C(11)—C(1) | 113.0(4) |
| C(12)—C(11)—H(11A) | 109.0 |
| C(1)—C(11)—H(11A) | 109.0 |
| C(12)—C(11)—H(11B) | 109.0 |
| C(1)—C(11)—H(11B) | 109.0 |
| H(11A)—C(11)—H(11B) | 107.8 |
| O(1)—C(12)—C(11) | 110.9(5) |
| O(1)—C(12)—H(12A) | 109.5 |
| C(11)—C(12)—H(12A) | 109.5 |
| O(1)—C(12)—H(12B) | 109.5 |
| C(11)—C(12)—H(12B) | 109.5 |
| H(12A)—C(12)—H(12B) | 108.0 |
| O(1)—C(13)—C(17) | 113.8(5) |
| O(1)—C(13)—C(14) | 107.0(5) |
| C(17)—C(13)—C(14) | 109.2(5) |
| O(1)—C(13)—H(13A) | 108.9 |
| C(17)—C(13)—H(13A) | 108.9 |
| C(14)—C(13)—H(13A) | 108.9 |
| C(13)—C(14)—C(15) | 112.7(5) |
| C(13)—C(14)—H(14A) | 109.1 |
| C(15)—C(14)—H(14A) | 109.1 |
| C(13)—C(14)—H(14B) | 109.1 |
| C(15)—C(14)—H(14B) | 109.1 |
| H(14A)—C(14)—H(14B) | 107.8 |
| N(1)—C(15)—C(14) | 109.7(5) |
| N(1)—C(15)—H(15A) | 109.7 |
| C(14)—C(15)—H(15A) | 109.7 |
| N(1)—C(15)—H(15B) | 109.7 |
| C(14)—C(15)—H(15B) | 109.7 |
| H(15A)—C(15)—H(15B) | 108.2 |
| C(17)—C(16)—N(1) | 109.9(4) |
| C(17)—C(16)—H(16A) | 109.7 |
| N(1)—C(16)—H(16A) | 109.7 |
| C(17)—C(16)—H(16B) | 109.7 |
| N(1)—C(16)—H(16B) | 109.7 |
| H(16A)—C(16)—H(16B) | 108.2 |
| C(16)—C(17)—C(13) | 113.1(5) |
| C(16)—C(17)—H(17A) | 109.0 |
| C(13)—C(17)—H(17A) | 109.0 |
| C(16)—C(17)—H(17B) | 108.9 |
| C(13)—C(17)—H(17B) | 108.9 |
| H(17A)—C(17)—H(17B) | 107.8 |
| N(1)—C(18)—H(18A) | 109.5 |
| N(1)—C(18)—H(18B) | 109.5 |
| H(18A)—C(18)—H(18B) | 109.5 |
| N(1)—C(18)—H(18C) | 109.5 |
| H(18A)—C(18)—H(18C) | 109.5 |
| H(18B)—C(18)—H(18C) | 109.5 |
| C(2)—C(19)—H(19A) | 120.0 |
| C(2)—C(19)—H(19B) | 120.0 |
| H(19A)—C(19)—H(19B) | 120.0 |
| C(10)—C(20)—H(20A) | 109.5 |
| C(10)—C(20)—H(20B) | 109.5 |
| H(20A)—C(20)—H(20B) | 109.5 |
| C(10)—C(20)—H(20C) | 109.5 |
| H(20A)—C(20)—H(20C) | 109.5 |
| H(20B)—C(20)—H(20C) | 109.5 |

-continued

| | |
|---|---|
| C(6)—C(21)—H(21A) | 109.5 |
| C(6)—C(21)—H(21B) | 109.5 |
| H(21A)—C(21)—H(21B) | 109.5 |
| C(6)—C(21)—H(21C) | 109.5 |
| H(21A)—C(21)—H(21C) | 109.5 |
| H(21B)—C(21)—H(21C) | 109.5 |
| O(3)—C(22)—C(6) | 110.9(4) |
| O(3)—C(22)—H(22A) | 109.5 |
| C(6)—C(22)—H(22A) | 109.5 |
| O(3)—C(22)—H(22B) | 109.5 |
| C(6)—C(22)—H(22B) | 109.4 |
| H(22A)—C(22)—H(22B) | 108.0 |
| O(3)—C(23)—O(2) | 111.7(4) |
| O(3)—C(23)—C(24) | 109.5(4) |
| O(2)—C(23)—C(24) | 107.5(4) |
| O(3)—C(23)—H(23A) | 109.4 |
| O(2)—C(23)—H(23A) | 109.4 |
| C(24)—C(23)—H(23A) | 109.4 |
| C(23)—C(24)—C(28) | 113.7(4) |
| C(23)—C(24)—C(25) | 114.2(5) |
| C(28)—C(24)—C(25) | 105.0(5) |
| C(23)—C(24)—H(24A) | 107.9 |
| C(28)—C(24)—H(24A) | 107.8 |
| C(25)—C(24)—H(24A) | 107.9 |
| C(24)—C(25)—C(26) | 107.1(5) |
| C(24)—C(25)—H(25A) | 110.3 |
| C(26)—C(25)—H(25A) | 110.3 |
| C(24)—C(25)—H(25B) | 110.3 |
| C(26)—C(25)—H(25B) | 110.3 |
| H(25A)—C(25)—H(25B) | 108.5 |
| C(27)—C(26)—C(25) | 104.5(5) |
| C(27)—C(26)—H(26A) | 110.9 |
| C(25)—C(26)—H(26A) | 110.9 |
| C(27)—C(26)—H(26B) | 110.9 |
| C(25)—C(26)—H(26B) | 110.9 |
| H(26A)—C(26)—H(26B) | 108.9 |
| C(28)—C(27)—C(26) | 107.0(6) |
| C(28)—C(27)—H(27A) | 110.3 |
| C(26)—C(27)—H(27A) | 110.3 |
| C(28)—C(27)—H(27B) | 110.3 |
| C(26)—C(27)—H(27B) | 110.3 |
| H(27A)—C(27)—H(27B) | 108.6 |
| C(27)—C(28)—C(24) | 105.2(5) |
| C(27)—C(28)—H(28A) | 110.7 |
| C(24)—C(28)—H(28A) | 110.7 |
| C(27)—C(28)—H(28B) | 110.7 |
| C(24)—C(28)—H(28B) | 110.7 |
| H(28A)—C(28)—H(28B) | 108.8 |
| C(30)—C(29)—C(34) | 118.8(5) |
| C(30)—C(29)—C(38) | 121.5(5) |
| C(34)—C(29)—C(38) | 119.8(5) |
| C(31)—C(30)—C(29) | 121.5(5) |
| C(31)—C(30)—H(30A) | 119.3 |
| C(29)—C(30)—H(30A) | 119.3 |
| C(30)—C(31)—C(32) | 120.7(5) |
| C(30)—C(31)—H(31A) | 119.6 |
| C(32)—C(31)—H(31A) | 119.6 |
| C(33)—C(32)—C(31) | 117.8(4) |
| C(33)—C(32)—C(35) | 123.6(4) |
| C(31)—C(32)—C(35) | 118.6(4) |
| C(32)—C(33)—C(34) | 121.4(4) |
| C(32)—C(33)—H(33A) | 119.3 |
| C(34)—C(33)—H(33A) | 119.3 |
| C(29)—C(34)—C(33) | 119.8(5) |
| C(29)—C(34)—H(34A) | 120.1 |
| C(33)—C(34)—H(34A) | 120.1 |
| O(4)—C(35)—O(5) | 123.5(4) |
| O(4)—C(35)—C(32) | 126.1(4) |
| O(5)—C(35)—C(32) | 110.4(4) |
| O(5)—C(36)—C(37) | 113.6(3) |
| O(5)—C(36)—C(36)#2 | 103.2(3) |
| C(37)—C(36)—C(36)#2 | 109.9(4) |
| O(5)—C(36)—H(36A) | 110.0 |
| C(37)—C(36)—H(36A) | 110.0 |
| C(36)#2—C(36)—H(36A) | 110.0 |
| O(7)—C(37)—O(6) | 127.0(4) |
| O(7)—C(37)—C(36) | 115.8(4) |
| O(6)—C(37)—C(36) | 117.1(4) |
| C(29)—C(38)—H(38A) | 109.5 |

| | |
|---|---|
| C(29)—C(38)—H(38B) | 109.5 |
| H(38A)—C(38)—H(38B) | 109.5 |
| C(29)—C(38)—H(38C) | 109.5 |
| H(38A)—C(38)—H(38C) | 109.5 |
| H(38B)—C(38)—H(38C) | 109.5 |

Twist Angle Values of the Compound of Formula (III-1)

| | |
|---|---|
| C(11)—C(1)—C(2)—C(19) | −14.3(8) |
| C(10)—C(1)—C(2)—C(19) | 116.4(7) |
| C(11)—C(1)—C(2)—C(3) | 170.5(5) |
| C(10)—C(1)—C(2)—C(3) | −58.7(6) |
| C(19)—C(2)—C(3)—C(4) | −120.5(7) |
| C(1)—C(2)—C(3)—C(4) | 54.9(7) |
| C(2)—C(3)—C(4)—C(5) | −53.9(6) |
| C(3)—C(4)—C(5)—C(10) | 58.5(6) |
| C(3)—C(4)—C(5)—C(6) | −165.9(4) |
| C(4)—C(5)—C(6)—C(22) | −55.9(5) |
| C(10)—C(5)—C(6)—C(22) | 77.2(5) |
| C(4)—C(5)—C(6)—C(7) | −178.3(4) |
| C(10)—C(5)—C(6)—C(7) | −45.1(5) |
| C(4)—C(5)—C(6)—C(21) | 64.2(5) |
| C(10)—C(5)—C(6)—C(21) | −162.7(4) |
| C(23)—O(2)—C(7)—C(8) | 75.8(5) |
| C(23)—O(2)—C(7)—C(6) | −52.7(5) |
| C(22)—C(6)—C(7)—O(2) | 49.6(5) |
| C(21)—C(6)—C(7)—O(2) | −66.7(5) |
| C(5)—C(6)—C(7)—O(2) | 175.5(3) |
| C(22)—C(6)—C(7)—C(8) | −77.8(5) |
| C(21)—C(6)—C(7)—C(8) | 165.9(4) |
| C(5)—C(6)—C(7)—C(8) | 48.1(5) |
| O(2)—C(7)—C(8)—C(9) | 176.6(4) |
| C(6)—C(7)—C(8)—C(9) | −56.6(5) |
| C(7)—C(8)—C(9)—C(10) | 60.5(5) |
| C(8)—C(9)—C(10)—C(5) | −55.1(5) |
| C(8)—C(9)—C(10)—C(20) | 70.7(5) |
| C(8)—C(9)—C(10)—C(1) | −170.6(4) |
| C(4)—C(5)—C(10)—C(9) | −177.6(4) |
| C(6)—C(5)—C(10)—C(9) | 48.8(5) |
| C(4)—C(5)—C(10)—C(20) | 59.0(5) |
| C(6)—C(5)—C(10)—C(20) | −74.7(5) |
| C(4)—C(5)—C(10)—C(1) | −60.0(5) |
| C(6)—C(5)—C(10)—C(1) | 166.4(4) |
| C(2)—C(1)—C(10)—C(9) | 176.4(4) |
| C(11)—C(1)—C(10)—C(9) | −53.9(5) |
| C(2)—C(1)—C(10)—C(5) | 59.0(5) |
| C(11)—C(1)—C(10)—C(5) | −171.2(4) |
| C(2)—C(1)—C(10)—C(20) | −63.7(5) |
| C(11)—C(1)—C(10)—C(20) | 66.0(5) |
| C(2)—C(11)—C(12) | −75.1(6) |
| C(10)—C(1)—C(11)—C(12) | 156.7(5) |
| C(13)—O(1)—C(12)—C(11) | −163.1(5) |
| C(1)—C(11)—C(12)—O(1) | −176.2(4) |
| C(12)—O(1)—C(13)—C(17) | −68.7(7) |
| C(12)—O(1)—C(13)—C(14) | 170.5(6) |
| O(1)—C(13)—C(14)—C(15) | 70.3(7) |
| C(17)—C(13)—C(14)—C(15) | −53.3(5) |
| C(18)—N(1)—C(15)—C(14) | 178.3(5) |
| C(16)—N(1)—C(15)—C(14) | −58.7(5) |
| C(13)—C(14)—C(15)—N(1) | 56.8(7) |
| C(15)—N(1)—C(16)—C(17) | 59.2(5) |
| C(18)—N(1)—C(16)—C(17) | −175.3(5) |
| N(1)—C(16)—C(17)—C(13) | −57.7(6) |
| O(1)—C(13)—C(17)—C(16) | −65.5(6) |
| C(14)—C(13)—C(17)—C(16) | 54.0(6) |
| C(23)—O(3)—C(22)—C(6) | 59.8(5) |
| C(7)—C(6)—C(22)—O(3) | −53.8(5) |
| C(21)—C(6)—C(22)—O(3) | 62.6(5) |
| C(5)—C(6)—C(22)—O(3) | −176.9(3) |
| C(22)—O(3)—C(23)—O(2) | −60.5(5) |
| C(22)—O(3)—C(23)—C(24) | −179.5(4) |
| C(7)—O(2)—C(23)—O(3) | 58.0(5) |
| C(7)—O(2)—C(23)—C(24) | 178.2(4) |
| O(3)—C(23)—C(24)—C(28) | −178.4(4) |
| O(2)—C(23)—C(24)—C(28) | 60.1(6) |
| O(3)—C(23)—C(24)—C(25) | −57.8(6) |
| O(2)—C(23)—C(24)—C(25) | −179.3(5) |
| C(23)—C(24)—C(25)—C(26) | −136.4(5) |
| C(28)—C(24)—C(25)—C(26) | −11.1(7) |
| C(24)—C(25)—C(26)—C(27) | −9.2(8) |
| C(25)—C(26)—C(27)—C(28) | 27.1(9) |
| C(26)—C(27)—C(28)—C(24) | −34.7(9) |
| C(23)—C(24)—C(28)—C(27) | 153.5(6) |
| C(25)—C(24)—C(28)—C(27) | 27.9(8) |
| C(34)—C(29)—C(30)—C(31) | −1.9(10) |
| C(38)—C(29)—C(30)—C(31) | 178.6(6) |
| C(29)—C(30)—C(31)—C(32) | 1.1(10) |
| C(30)—C(31)—C(32)—C(33) | 0.4(8) |
| C(30)—C(31)—C(32)—C(35) | 179.3(5) |
| C(31)—C(32)—C(33)—C(34) | −1.0(6) |
| C(35)—C(32)—C(33)—C(34) | −179.9(4) |
| C(30)—C(29)—C(34)—C(33) | 1.2(8) |
| C(38)—C(29)—C(34)—C(33) | −179.3(5) |
| C(32)—C(33)—C(34)—C(29) | 0.2(7) |
| C(36)—O(5)—C(35)—O(4) | −2.5(6) |
| C(36)—O(5)—C(35)—C(32) | 177.6(3) |
| C(33)—C(32)—C(35)—O(4) | 175.7(5) |
| C(31)—C(32)—C(35)—O(4) | −3.1(7) |
| C(33)—C(32)—C(35)—O(5) | −4.4(6) |
| C(31)—C(32)—C(35)—O(5) | 176.7(4) |
| C(35)—O(5)—C(36)—C(37) | −75.8(5) |
| C(35)—O(5)—C(36)—C(36)#2 | 165.2(4) |
| O(5)—C(36)—C(37)—O(7) | 177.7(4) |
| C(36)#2—C(36)—C(37)—O(7) | −67.2(4) |
| O(5)—C(36)—C(37)—O(6) | −0.6(6) |
| C(36)#2—C(36)—C(37)—O(6) | 114.5(4) |

Experimental Example 1: Solid Stability Test of Crystal Form A Under High Temperature and High Humidity Conditions Approximately 100 mg of Crystal Form A was weighed in duplicate, placed at the bottom of a glass vial, and spread into a thin layer. The vial was sealed with aluminum-foil paper which was punched to generate some small holes to ensure that the sample could fully contact with the ambient air. The vial was placed in a chamber with a constant temperature and humidity of 40° C. and 75%. Samples were placed under the above conditions and tested on day 5 and day 10. The test results were compared with the initial test results as measured on day 0. Test results are shown in Table-2 below.

TABLE 2

Solid Stability Test of Crystal Form A

| Time point (day) | Appearance | Crystal form | Purity (%) | Total impurities (%) |
|---|---|---|---|---|
| 0 | Off-white powder | Crystal Form A | 98.51 | 1.49 |
| 5 | Off-white powder | Crystal Form A | 98.37 | 1.61 |
| 10 | Off-white powder | Crystal Form A | 98.45 | 1.55 |

Experimental conclusion: the crystal form of the present disclosure had good stability and was easy to be prepared into a medicine.

Experimental Example 2: Solid Physical Stability Test of Crystal Form A Under Different Temperature, Humidity, and Light Conditions Approximately 100 mg of Crystal Form A was weighed in duplicate, placed at the bottom of a glass vial, and spread into a thin layer. The vial was sealed with aluminum-foil paper which was punched to generate some small holes to ensure that the sample could fully contact with the ambient air. The 4 samples as prepared were placed under conditions of 25° C./92.5% relative humidity, 60° C., 40° C./75%, and light. The physical stability of the samples on day 10 was examined. Meanwhile, approximately 100 mg of Crystal Form A as a solid was additionally weighed, placed at the bottom of a glass vial, sealed with a screw cap, and stored at −20° C. for use as a control. On day 10, all samples were taken and returned to room temperature. The appearance change of the samples was observed, and the crystal form of the samples was examined by XRPD. The solid physical stability of Crystal Form A of the compound of Formula (II) was determined by comparing the accelerated samples with the control sample. Results of the physical stability test of Crystal Form A as a solid were shown in Table-3 below.

TABLE 3

Solid Physical Stability Test of Crystal Form A under Different Temperature, Humidity, and Light Conditions

| Investigation item | Time point | Day 0 (stored at −20° C. in a confined space) (as a control sample) | 25° C./ 92.5% relative humidity (open) | 60° C. (open) | 40° C./ 75% relative humidity (open) | light |
|---|---|---|---|---|---|---|
| Crystal form | Day 10 | Crystal Form A | Crystal Form A | Crystal Form A | Crystal Form A | Crystal Form A |
| Characters | Day 10 | Off-white powder | Off-white powder | Off-white powder | Off-white powder | Off-white powder |

Experimental Example 3: Study on Polymorphism of the Compound of Formula (II)

The compound of Formula (II) was dissolved in a corresponding solvent and stirred at 40° C. for 2 days in the dark. The solution was then centrifuged to obtain a precipitate which was dried and subjected to XRPD detection. The results are shown in Table 4 below.

TABLE 4

Study on Polymorphism of the Compound of Formula (II)

| No. | Solvent | Crystal form |
|---|---|---|
| 1 | Methanol | Crystal Form A |
| 2 | Ethanol | Crystal Form A |

As can be seen from the table above, the Crystal Form A of the compound of Formula (II) was stable under conditions of the above solvents.

Biochemical Test 1: Release of IL-6 from THP-1 Cells

Purpose:
Evaluate the inhibitory effect of the compound on LPS-induced release of IL-6 from THP-1 cells by measuring the level of IL-6 in the cell culture supernatant.

Materials:
Cell line: THP-1 cell line
THP-1 cell culture medium (RPMI 1640, Gibco #22400-089, 10% serum Gibco #10099-141)
LPS, 1 mg/ml (Sigma #L5293)
DPBS (Hyclone, #SH30028.01B)
Human IL-6 CBA kit, BD #558276
CBA Human Soluble Protein Master Buffer Kit, BD #558265
Dexamethasone: J&K #308890
96-well cell plate, Corning #
$CO_2$ incubator, Thermo #371
Centrifuge, Eppendorf #5810R
Vi-cell Cell Counter, Beckman Coulter
FACSCalibur, BD #97500540

Experimental Procedures and Methods:
a) Cell Plating
 1) The medium was pre-heated in a 37° C. water bath;
 2) The cell suspension in the culture flask was mixed well, transferred to a centrifuge tube, and centrifuged at 1200 rpm for 5 minutes at room temperature. The supernatant was discarded, and culture medium was added to a volume of 10 ml to re-suspend the cell pellets;
 3) 1 mL of the cell resuspension was pipetted and counted with Vi-cell;
 4) THP-1 cells were diluted with culture medium to $5 \times 10^5$ cells/mL and the diluted cells were added to a 96-well plate (100 μl/well, $5 \times 10^5$ cells/well);
b) Compound Loading:
 1) The compound was dissolved in DMSO to give a solution of 30 mM, and then the solution was 3-fold diluted with DMSO into 4 gradients, which were 30 mM, 10 mM, 3 mM, and 1 mM, respectively. For each gradient, 4 μl of the solution was added to 1 ml of culture medium to form a mixture with a concentration of 120 uM, 40 uM, 12 uM, or 4 uM, respectively. Then, 50 ul of the mixture was added to a well containing cells to a final concentration of 30 uM, 10 uM, 3 uM, or 1 uM, respectively. Dexamethasone was added as a positive drug to a separate well containing cells at a final concentration of 100 nM.
c) Cell Stimulation
 1 mg/ml of a LPS solution was diluted to 800 ng/ml with culture medium, and the diluted solution was added to the cell culture well at 50 ul per well.
d) Cell Incubation and Detection
 The cell culture plate was placed in a 37° C. incubator and incubated for 24 hours. Then, the supernatant was collected, and the level of IL-6 therein was detected by CBA. The experimental results are shown in Table 5:

TABLE 5

Results of inflammatory factor IL-6 detected by CBA - inhibition rate @10 uM

| Test sample | Inhibition rate @10 uM |
|---|---|
| Compound h | A |

Note:
A > 60%;
Conclusion: Compound h had a significant inhibitory effect on inflammatory factor IL-6.

Biochemical Test 2: Release of Cytokines Involved in the Th1 Pathway Such as TNF-α and IL-6 from Mouse Spleen Cells Purpose:
Evaluate the inhibitory effect of the compound on LPS-induced release of cytokines involved in the Th1 pathway such as TNF-α and IL-6 from mouse spleen cells by measuring the levels of the cytokines involved in the Th1 pathway such as TNF-α and IL-6 in the culture supernatant of mouse spleen cells.

Experimental Materials:
Cells: spleen cells isolated from the spleens of normal C57BL/6 mice
Culture medium for mouse spleen cells (RPMI 1640, Gibco #22400-089, 10% serum Gibco #10099-141)
Erythrocyte lysis buffer, Gibco A10492-01
LPS, Sigma #L2630
DPBS, Hyclone, #SH30028.01B
Mouse TNF-α CBA kit, BD #558299
Mouse IL-6 CBA kit, BD #558310
CBA Mouse Soluble Protein Master Buffer Kit, BD 558267
Dexamethasone: J&K #308890
Pirfenidone: TA00720266
96-well cell plate, Costar 3799
$CO_2$ incubator, Thermo #371
Centrifuge, Eppendorf #5810R
Vi-cell Cell Counter, Beckman Coulter
BD FACSCanto II Flow Cytometer, 338962

Experimental Procedures and Methods:
a) Isolation and Plating of Mouse Spleen Cells
1) The mice were sacrificed under aseptic conditions, and the spleens were collected and ground in a filter having a pore size of 70 μm. The obtained cell suspension was collected.
2) The cell suspension was transferred to a centrifuge tube, where it was centrifuged at 1200 rpm at room temperature for 5 minutes, and the supernatant was discarded;
3) Erythrocyte lysis buffer was added at a ratio of 5 mL/spleen. The cells were re-suspended and allowed to stand for 5 minutes;
4) 3 volumes of DPBS were added to the cell suspension. The mixture was centrifuged at 1200 rpm at room temperature for 5 minutes, and the supernatant was discarded;
5) The cells were re-suspended and counted with Vi-cell. Then, the cells were adjusted to a concentration of $1 \times 10^6$/mL;
6) The cells were added to a 96-well plate (100 μL/well, $1 \times 10^5$ cells/well);
b) Cell stimulation
LPS was formulated with culture medium into a 4 μg/ml solution, and then the solution was added to the cell culture well at 50 μl per well.
c) Compound Loading:
The compound was dissolved in DMSO to give a solution of 100 mM, and then the solution was diluted with DMSO to obtain 3 gradients, which were 30 mM, 10 mM, and 3 mM, respectively. For each gradient, 4 μl of the solution was added to 1 ml of culture medium to form a mixture with a concentration of 120 μM, 40 μM, or 12 μM, respectively. 50 μl of the mixture was added to a corresponding well to a final concentration of 30 μM, 10 μM, or 3 μM, respectively. Dexamethasone was added as a positive drug to a separate well containing cells at a final concentration of 100 nM. Pirfenidone was added as a reference compound to a separate well containing cells at a final concentration of 500 μM.
d) Cell Incubation and Detection
The cell culture plate was placed in a 37° C. incubator and incubated for 24 hours. Then, the supernatant was collected, and the levels of TNF-α and IL-6 therein were detected by CBA.

Biochemical Test 3: Release of Cytokines Involved in the Th1 Pathway Such as IFN-γ and IL-2 from Mouse Spleen Cells Purpose:
Evaluate the inhibitory effect of the compound on the release of cytokines involved in the Th1 pathway such as IFN-γ and IL-2 from mouse spleen cells by measuring the levels of cytokines involved in the Th1 pathway such as IFN-γ and IL-2 in the culture supernatant of mouse spleen cells.

Experimental Materials:
Cells: spleen cells isolated from the spleens of normal C57BL/6 mice
Culture medium for mouse spleen cells (RPMI 1640, Gibco #22400-089, 10% serum Gibco #10099-141)
Erythrocyte lysis buffer, Gibco A10492-01
Anti-mouse CD3 antibody, BD 553057
DPBS, Hyclone, #SH30028.01B
Mouse IFN-γ CBA kit, BD #558296
Mouse IL-2 CBA kit, BD #558310 558297
CBA Mouse Soluble Protein Master Buffer Kit, BD 558267
Dexamethasone: J&K #308890
Pirfenidone: TA00720266
96-well cell plate, Costar 3599
$CO_2$ incubator, Thermo #371
Centrifuge, Eppendorf #5810R
Vi-cell Cell Counter, Beckman Coulter
BD FACSCanto II Flow Cytometer, 338962

Experimental Procedures and Methods:
a) Anti-Mouse CD3 Antibody Coating
The anti-mouse CD3 antibody diluted to 5 μg/mL with DPBS was added to a 96-well plate at 100 μL/well. The culture plate was allowed to stand at 4° C. overnight;
b) Isolation and Plating of Mouse Spleen Cells
1) The mice were sacrificed under aseptic conditions, and the spleens were collected and ground in a filter having a pore size of 70 μm. The obtained cell suspension was collected.
2) The cell suspension was transferred to a centrifuge tube, where it was centrifuged at 1200 rpm at room temperature for 5 minutes, and the supernatant was discarded;
3) Erythrocyte lysis buffer was added at a ratio of 5 mL/spleen. The cells were re-suspended and allowed to stand for 5 minutes;
4) 3 volumes of DPBS were added to the cell suspension. The mixture was centrifuged at 1200 rpm at room temperature for 5 minutes, and the supernatant was discarded;
5) The cells were re-suspended and counted with Vi-cell. Then, the cells were adjusted to a concentration of $1 \times 10^6$/mL;
c) Cell Stimulation
1) The 96-well plate was removed from 4° C. and washed twice with DPBS;
2) The cells were added to the wells coated with the anti-mouse CD3 antibody at 50 μL/well, i.e. $1 \times 10^5$ cells/well; and meanwhile, the cells were added to un-coated wells in the same amount, as a negative control;
d) Compound Loading:
The compound was dissolved in DMSO to give a solution of 100 mM, and then the solution was diluted with DMSO to obtain 3 gradients, which were 30 mM, 10 mM, and 3 mM, respectively. For each gradient, 4 μl of the solution was added to 1 ml of culture medium to form a mixture with a concentration of 120 μM, 40 μM, or 12 μM, respectively. 50 μl of the mixture was added to a corresponding well to a final concentration of 30 μM, 10 μM, or 3 μM, respectively.

Dexamethasone was added as a positive drug to a separate well with cells at a final concentration of 100 nM. Pirfenidone was added as a reference compound to a separate well containing cells at a final concentration of 500 μM.

e) Cell Incubation and Detection

The cell culture plate was placed in a 37° C. incubator and incubated for 24 hours. Then, the supernatant was collected, and the levels of IFN-γ and IL-2 therein were detected by CBA.

Biochemical Test 4: Release of Cytokines Involved in the Th2 Pathway Such as IL-13 from Mouse Spleen Cells Purpose:

Evaluate the inhibitory effect of the compound on LPS-induced release of cytokines involved in the Th2 pathway such as IL-13 from mouse spleen cells by measuring the levels of cytokines involved in the Th2 pathway such as IL-13 in the culture supernatant of mouse spleen cells.

Experimental Materials:

Cells: CD4+ cells isolated and sorted from the spleens of normal C57BL/6 mice

Cell culture medium (RPMI 1640, Gibco #22400-089, 10% serum Gibco #10099-141)

Erythrocyte lysis buffer

Anti-mouse CD3 antibody, BD 553057

Anti-mouse IFNγ antibody, BD 554430

Anti-mouse IL-12 antibody, BD 553375

Mouse IL-4, PeproTech 214-14

Mouse CD4+ T Cell Isolation Kit, STEMCELL 19852A

DPBS, Hyclone, #SH30028.01B

Mouse IL-13 CBA kit, BD 558349

CBA Mouse Soluble Protein Master Buffer Kit, BD 558267

Dexamethasone: J&K #308890

Pirfenidone: TA00720266

96-well cell plate, Costar 3599

$CO_2$ incubator, Thermo #371

Centrifuge, Eppendorf #5810R

Vi-cell Cell Counter, Beckman Coulter

BD FACSCanto II Flow Cytometer, 338962

Experimental Procedures and Methods:

a) Anti-Mouse CD3 Antibody Coating

The anti-mouse CD3 antibody diluted to 5 μg/mL with DPBS was added to a 96-well plate at 100 μL/well. The culture plate was allowed to stand at 4° C. overnight;

b) Isolation and Plating of Mouse Spleen CD4+ T Cells

1) The mice were sacrificed under aseptic conditions, and the spleens were collected and ground in a filter having a pore size of 70 μm. The obtained cell suspension was collected.

2) The cell suspension was transferred to a centrifuge tube, where it was centrifuged at 1200 rpm at room temperature for 5 minutes, and the supernatant was discarded;

3) Erythrocyte lysis buffer was added at a ratio of 5 mL/spleen. The cells were re-suspended and allowed to stand for 5 minutes;

4) 3 volumes of DPBS were added to the cell suspension. The mixture was centrifuged at 1200 rpm at room temperature for 5 minutes, and the supernatant was discarded;

5) The cells were re-suspended and counted with Vi-cell. Then, the cells were adjusted to a concentration of $1\times10^8$/mL;

6) CD4+ T cells were isolated by using the Mouse CD4+ T Cell Isolation Kit, and the isolated cells were adjusted to a concentration of $1\times10^6$/mL;

7) The 96-well plate that had been coated overnight was removed from 4° C. and washed twice with DPBS;

8) The isolated CD4+ T cells were added to the wells coated with the anti-CD3 antibody at 50 μL/well, i.e. $1\times10^5$ cells/well; and meanwhile, the CD4+ T cells were added to un-coated wells in the same amount, as a negative control;

c) Induction of Th2 Cells

The mouse anti-IFNγ antibody and anti-IL-12 antibody were simultaneously added to the culture medium both at a concentration of 40 μg/mL, and mouse IL-4 was added thereto at a concentration of 40 ng/mL. An induction solution was prepared and added to the wells that had been plated with cells and coated with anti-CD3 antibody at 50 μL/well. Three wells were left without the addition of the induction solution and used as a control;

d) Compound Loading:

The compound was dissolved in DMSO to give a solution of 100 mM, and then the solution was diluted with DMSO to obtain 3 gradients, which were 30 mM, 10 mM, and 3 mM, respectively. For each gradient, 4 μl of the solution was added to 1 ml of culture medium to form a mixture with a concentration of 120 μM, 40 μM, or 12 μM, respectively. 50 μl of the mixture was added to a corresponding well to a final concentration of 30 μM, 10 μM, or 3 μM, respectively. Dexamethasone was added as a positive drug to a separate well containing cells at a final concentration of 100 nM. Pirfenidone was added as a reference compound to a separate well containing cells at a final concentration of 500 μM.

e) Cell Incubation and Detection

The cell culture plate was placed in a 37° C. incubator and incubated for 72 hours. Then, the supernatant was collected, and the level of IL-13 therein was detected by CBA.

Biochemical Test 5: Release of TGF-β from Mouse Peritoneal Macrophages

Purpose:

Evaluate the inhibitory effect of the compound on the release of TGF-β from mouse peritoneal macrophages by measuring the level of TGF-β in the culture supernatant of mouse peritoneal macrophages.

Experimental Materials:

Cells: Macrophages collected by peritoneal lavage of normal Balb/c mice

Cell culture medium (RPMI 1640, Gibco #22400-089, 10% serum Gibco #10099-141)

Mouse TNF-α, PeproTech 315-01A

Mouse IL-4, PeproTech 214-14

DPBS, Hyclone, #SH30028.01B

Mouse TGF-β ELISA kit, R&D MB100B

Dexamethasone: J&K #308890

Pirfenidone: TA00720266

48-well cell plate, Costar 3548

$CO_2$ incubator, Thermo #371

Centrifuge, Eppendorf #5810R

Vi-cell Cell Counter, Beckman Coulter

Microplate reader, Molecular Devices SpectraMax i3

Experimental Procedures and Methods:

a) Harvesting and Plating of Mouse Peritoneal Macrophages

1) The mice were sacrificed under aseptic conditions, and the abdominal skin was cut open to expose the abdominal wall;

2) 5 mL of serum-free RPMI 1640 medium was pipetted with a 5 mL syringe. The abdominal wall was gently lifted away with tweezers by one hand, and the culture medium was slowly injected into the abdominal cavity with syringe by another hand;

3) After the abdominal cavity was fully flushed with the culture medium, the culture medium in the abdominal cavity was slowly aspirated with a syringe and transferred to a centrifuge tube;

4) The obtained cell suspension was centrifuged at 1200 rpm at room temperature for 5 minutes, and the supernatant was discarded;

5) The cells were re-suspended in culture medium containing 10% serum, plated in a Petri dish, and incubated at 37° C. for 2 hours. Then the suspended cells were washed away with DPBS;

6) The adherent macrophages were blown down with culture medium and counted with Vi-Cell. Then the cells were adjusted to a concentration of $1.6 \times 10^6$/mL;

7) The macrophages were added to a 48-well plate at 250 μL/well, i.e. $4 \times 10^5$ cells/well;

b) Cell Stimulation:

1) After the cells were attached to the wall, the culture medium was replaced with serum-free RPMI 1640 medium, 250 μL/well;

2) A stimulating solution containing TNFα and IL-13 both at a concentration of 80 ng/mL was prepared with serum-free medium, and added to the wells plated with cells at 125 μL/well. Three wells were left without the addition of the stimulating solution and used as a blank control;

c) Compound Loading:

The compound was dissolved in DMSO to give a solution of 100 mM, and then the solution was diluted with DMSO to obtain 3 gradients, which were 30 mM, 10 mM, and 3 mM, respectively. For each gradient, 4 μl of the solution was added to 1 ml of culture medium to form a mixture with a concentration of 120 μM, 40 μM, or 12 μM, respectively. 125 μl of the mixture was added to a corresponding well to a final concentration of 30 μM, 10 μM, or 3 μM, respectively. Dexamethasone was added as a positive drug to a separate well containing cells at a final concentration of 100 nM. Pirfenidone was added as a reference compound to a separate well containing cells at a final concentration of 500 μM.

e) Cell Incubation and Detection

The cell culture plate was placed in a 37° C. incubator and incubated for 24 hours. Then, the supernatant was collected, and the level of TGF-β therein was detected by ELISA.

The results of in vitro cytokine screening of biochemical tests 2~5 are shown in Table 6.

TABLE 6

In vitro cytokine screening results for the compound of Formula (II)

| Pathway | Cytokine | Inhibition rate |
|---|---|---|
| Th1 | IL-6 | 48%@10 μM |
|  | TNF-α | 40.3%@30 μM |
|  | IFN-γ | 85.3%@10 μM |
|  | IL-2 | 78.2%@10 μM |

TABLE 6-continued

In vitro cytokine screening results for the compound of Formula (II)

| Pathway | Cytokine | Inhibition rate |
|---|---|---|
| Th2 | IL-13 | 99.9%@10 μM |
|  | Fibrosis factor TGF-β | 51.0%@10 μM |

Conclusion: The compound of Formula (II) had an obvious inhibitory effect on cytokines involved in Th1- and Th2-related pathways and the fibrosis factor TGF-β.

In Vivo Efficacy Test Results:

It was shown by a SD rat model of left unilateral pulmonary fibrosis that the compound of Formula (II) had a significant inhibitory effect on IPF.

The invention claimed is:

1. A crystal Form A of a compound of Formula (II);
having an X-ray powder diffraction pattern comprising characteristic diffraction peaks at 2θ angles of: 10.00±0.2°, 12.91±0.2°, and 16.27±0.2°.

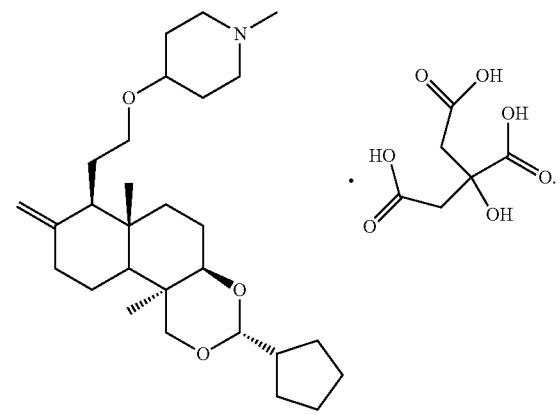

(II)

2. The Crystal Form A according to claim 1, which has an X-ray powder diffraction pattern comprising characteristic diffraction peaks at 2θ angles of: 5.05±0.2°, 10.00±0.2°, 12.91±0.2°, 13.42±0.2°, 14.51±0.2°, 14.94±0.2°, 16.27±0.2°, and 18.36±0.2°.

3. The Crystal Form A according to claim 2, which has an XRPD pattern as shown in FIG. 1.

4. The Crystal Form A according to claim 1, which has a differential scanning calorimetry curve comprising endothermic peaks at 119.27° C.±3° C. and 144.42° C.±3° C.

Figure 2:
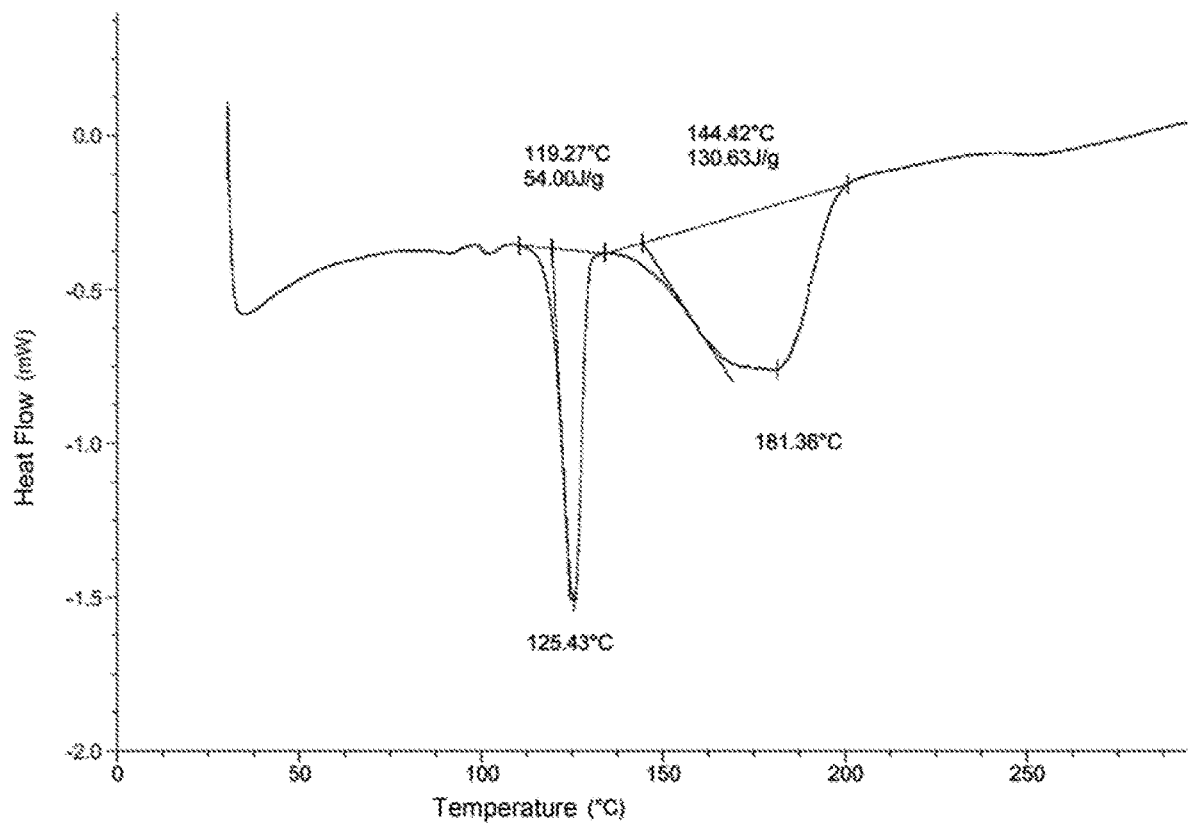
FIG. 2 shows the DSC spectrum of Crystal Form A of the compound of Formula (II)

5. The Crystal Form A according to claim 4, which has a DSC pattern as shown in FIG. 2.

6. The Crystal Form A according to claim 1, which has a thermogravimetric analysis curve showing a weight loss of 0.1268%±0.1% at 120.00° C. ±3° C.

Figure 3:
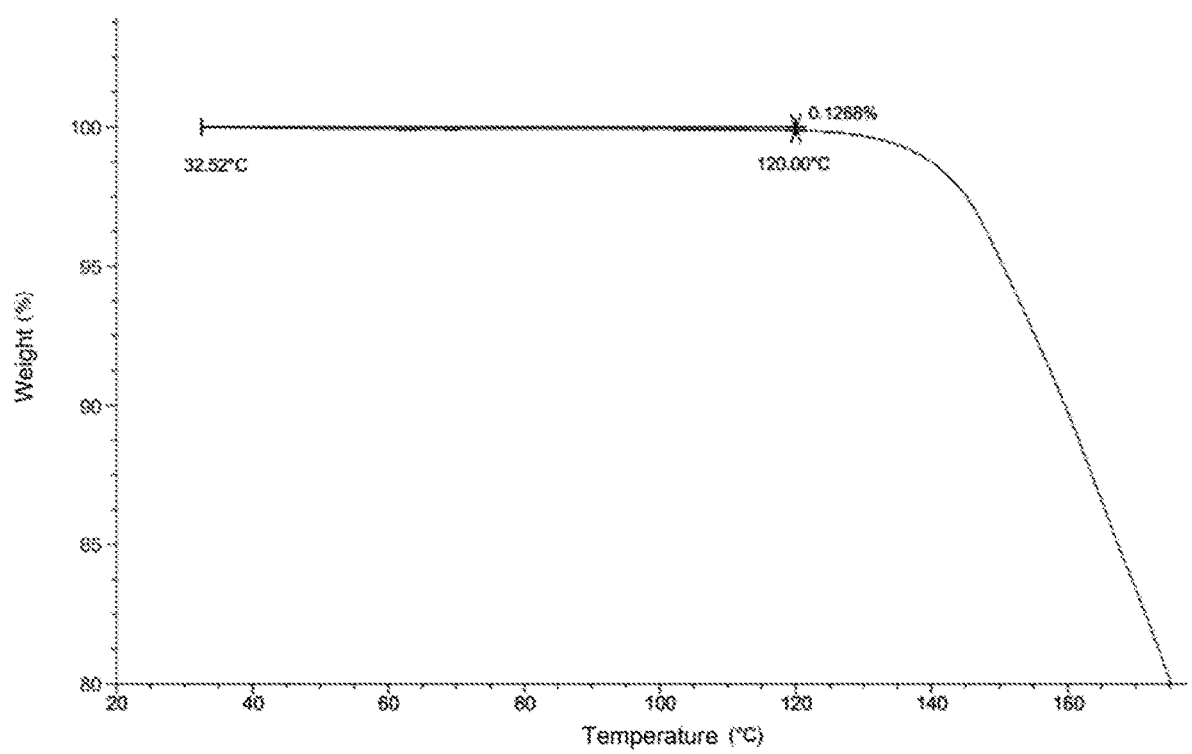
FIG. 3 shows the TGA spectrum of Crystal Form A of the compound of Formula (II)
Figure 4:
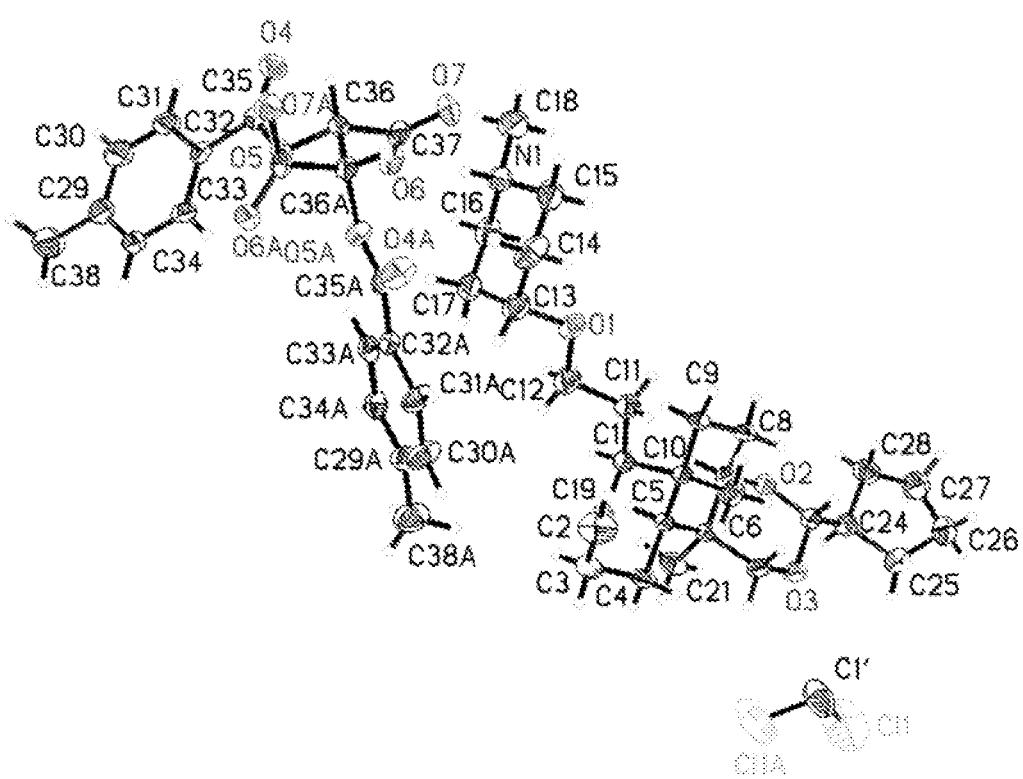
FIG. 4 shows the stereostructure ellipsoid of a single molecule of the compound of Formula (III-1) comprising one molecule of a dichloromethane solvent.
Figure 5:
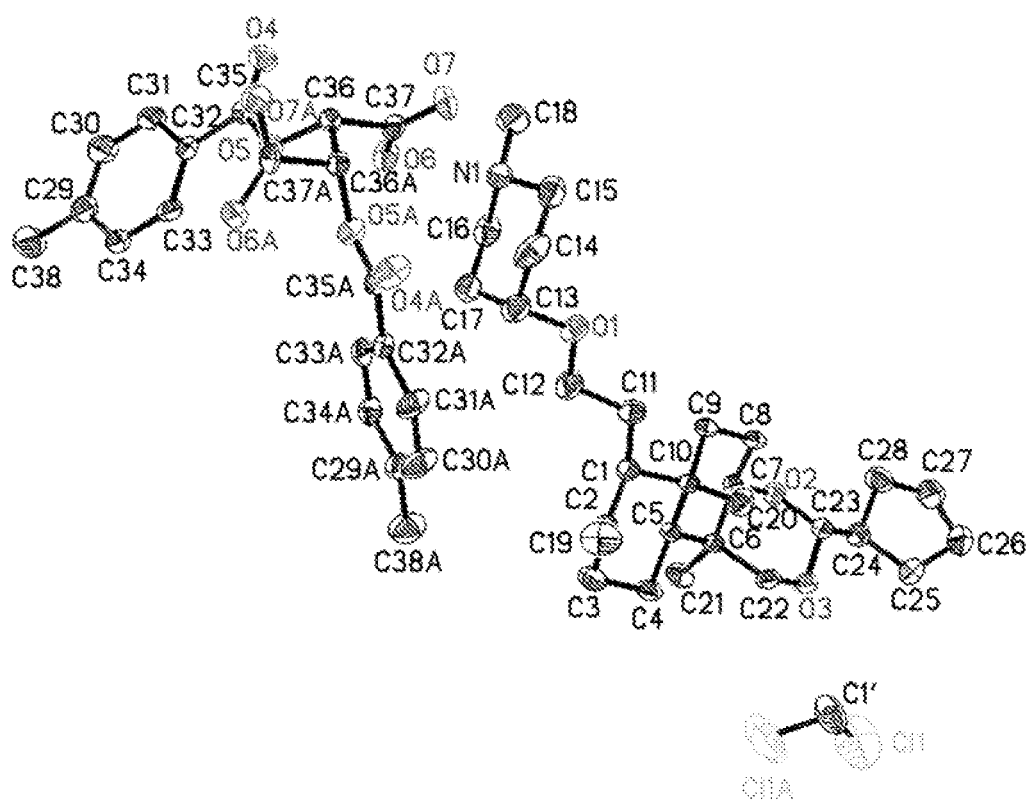
FIG. 5 shows the stereostructure ellipsoid of a bi-molecule of the compound of Formula (III-1) comprising one molecule of a dichloromethane solvent.
Figure 6:
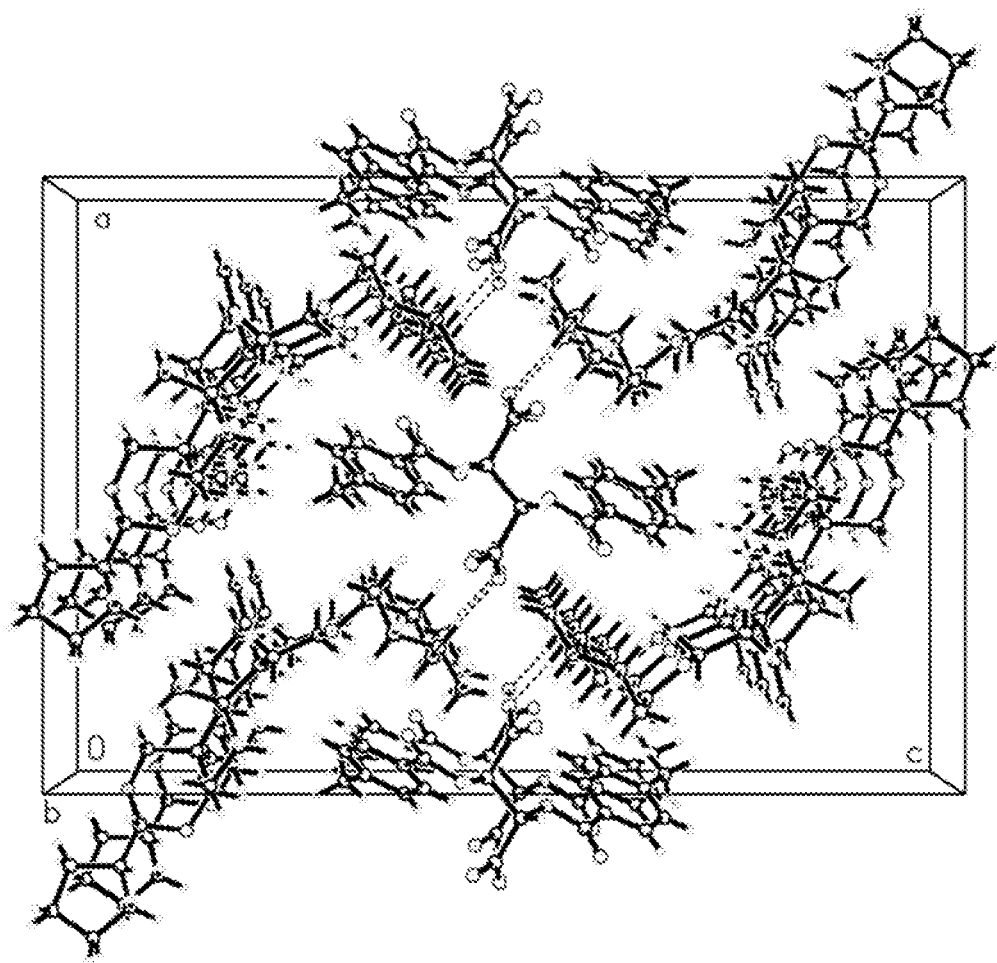
FIG. 6 shows the crystal stacking diagram of the compound of Formula (III-1) comprising one molecule of a dichloromethane solvent along the a-axis direction.

7. The Crystal Form A according to claim 6, which has a TGA pattern as shown in FIG. 3.

* * * * *